(12) United States Patent
Stinchcomb et al.

(10) Patent No.: US 10,238,648 B2
(45) Date of Patent: Mar. 26, 2019

(54) ABUSE DETERRENT OPIOID/OPIOID-ANTAGONIST TRANSDERMAL PATCH

(71) Applicant: BUZZZ PHARMACEUTICALS LIMITED, Dublin (IE)

(72) Inventors: Audra Lynn Stinchcomb, Ruxton, MD (US); Dana Carmel Hammell, Georgetown, KY (US); Stan Lee Banks, Cincinnati, OH (US); Josh Eldridge, Miami, FL (US); Miroslaw Jerzy Golinski, Lexington, KY (US)

(73) Assignee: BUZZZ PHARMACEUTICALS LTD., Dublin (IE)

( * ) Notice: Subject to any disclaimer, the term of this patent is extended or adjusted under 35 U.S.C. 154(b) by 0 days.

(21) Appl. No.: 15/326,797

(22) PCT Filed: Jul. 17, 2015

(86) PCT No.: PCT/EP2015/066457
§ 371 (c)(1),
(2) Date: Jan. 17, 2017

(87) PCT Pub. No.: WO2016/009064
PCT Pub. Date: Jan. 21, 2016

(65) Prior Publication Data
US 2017/0209429 A1  Jul. 27, 2017

Related U.S. Application Data

(60) Provisional application No. 62/187,473, filed on Jul. 1, 2015, provisional application No. 62/026,195, filed on Jul. 18, 2014.

(51) Int. Cl.
| | |
|---|---|
| A61K 9/00 | (2006.01) |
| A61K 9/70 | (2006.01) |
| A61K 47/10 | (2017.01) |
| A61K 47/12 | (2006.01) |
| A61K 47/14 | (2017.01) |
| A61K 47/32 | (2006.01) |
| A61K 47/38 | (2006.01) |
| A61K 31/485 | (2006.01) |

(52) U.S. Cl.
CPC .......... *A61K 31/485* (2013.01); *A61K 9/0014* (2013.01); *A61K 9/7053* (2013.01); *A61K 9/7061* (2013.01); *A61K 9/7069* (2013.01); *A61K 9/7084* (2013.01); *A61K 9/7092* (2013.01); *A61K 47/10* (2013.01); *A61K 47/12* (2013.01); *A61K 47/14* (2013.01); *A61K 47/32* (2013.01); *A61K 47/38* (2013.01)

(58) Field of Classification Search
CPC ...... A61K 31/485; A61K 47/12; A61K 47/32; A61K 47/38; A61K 9/0014; A61K 9/7053; A61K 9/7061; A61K 9/7069; A61K 9/7092
See application file for complete search history.

(56) References Cited

U.S. PATENT DOCUMENTS

| | | | |
|---|---|---|---|
| 4,584,355 A | 4/1986 | Blizzard | |
| 4,585,836 A | 4/1986 | Homan | |
| 4,591,622 A | 5/1986 | Blizzard | |
| 4,655,767 A | 4/1987 | Woodard | |
| 5,149,538 A | 9/1992 | Granger et al. | |
| 5,232,702 A | 8/1993 | Pfister | |
| 5,262,165 A | 11/1993 | Govil et al. | |
| 5,474,783 A | 12/1995 | Miranda | |
| 5,762,952 A | 6/1998 | Barnhart | |
| 5,916,587 A * | 6/1999 | Min | A61K 9/7061 424/448 |
| 5,985,317 A | 11/1999 | Venkateshwaran | |
| 6,139,866 A | 10/2000 | Chono | |
| 6,231,885 B1 | 5/2001 | Carrara | |
| 2003/0060479 A1 | 3/2003 | Brown | |
| 2004/0013716 A1* | 1/2004 | Gale | A61K 31/4535 424/449 |
| 2004/0033254 A1* | 2/2004 | Song | A61K 9/7053 424/449 |
| 2004/0126323 A1* | 7/2004 | Shevchuk | A61K 9/7069 424/10.1 |
| 2008/0233178 A1 | 9/2008 | Reidenberg et al. | |
| 2011/0244022 A1 | 10/2011 | Cottrell et al. | |
| 2011/0245783 A1 | 10/2011 | Stinchcomb et al. | |
| 2013/0251760 A1 | 9/2013 | Gale et al. | |
| 2017/0202830 A1 | 7/2017 | Stinchcomb et al. | |

FOREIGN PATENT DOCUMENTS

| | | |
|---|---|---|
| EP | 1381352 B1 | 6/2007 |
| WO | 2005081825 | 9/2005 |
| WO | 2014012653 | 1/2014 |
| WO | 2016009063 | 1/2016 |

OTHER PUBLICATIONS

Dyson, D. H. et al., "Reversal of Oxymorphone Sedation by Naloxone, Nalmefene, and Butorphanol," Vet. Surg. 1990, 19, 398-403.
Third party submission submitted in U.S. Appl. No. 15/326,784, mailed Aug. 24, 2017.
PCT International Search Report and Written Opinion completed by the ISA/EP dated Sep. 23, 2015 and issued in connection with PCT/EP2015/066457, 11 pages.

(Continued)

*Primary Examiner* — Michael B. Pallay
(74) *Attorney, Agent, or Firm* — Barnes & Thornburg LLP

(57) ABSTRACT

An abuse deterrent transdermal patch comprising a multilaminate. The multilaminate can comprise a first layer comprising an opioid analgesic compound, or a pharmaceutically acceptable salt thereof, and a pharmaceutically acceptable pressure sensitive adhesive. The multilaminate can further comprise a second layer comprising an opioid antagonist, or a pharmaceutically acceptable salt thereof, and a pharmaceutically acceptable adhesive. In addition, the multilaminate can further comprise a barrier layer disposed between the first and second layers.

21 Claims, 24 Drawing Sheets

(56) References Cited

OTHER PUBLICATIONS

Satas, Donatas, Handbook of pressure sensitive adhesive technology, book, 1989, pp. 396-456, Van Nostrand Reinhold, New York, U.S.A.

Satas, Donatas, Handbook of pressure sensitive adhesive technology, book, 1989, pp. 508-517, Van Nostrand Reinhold, New York, U.S.A.

Rowe, Raymond C., Handbook of Pharmaceutical Excipients, 5th edition, 2006, pp. 494-497, Pharmaceutical Press, Great Britian, and the American Pharmacists Association, NW Washington D.C., U.S.A.

Pathan, Inayat Bashir, Chemical Penetration Enhancers of Transdermal Drug Delivery Systems, Tropical Journal of Pharmaceutical Research, Jun. 2009, pp. 173-179, vol. 8, No. 2.

Karande, Pankaj, Enhancement of transdermal drug delivery via synergistic action of chemicals, Biochimica et Biophysica Acta, Sep. 2009, pp. 236-2373, vol. 1788, Issue 11.

Ogiso, Taro, Effect of Various Enhancers on Transdermal penetration of Indomethacin and Urea, and Relationship between Penetration Parameters and Enhancement Factors, Journal of Pharmaceutical Sciences, Apr. 1995, pp. 482-488, vol. 84, No. 4.

Francoeur, Michael L., Oleic Acid: Its Effects on Stratum Corneum in Relation to (Trans)Dermal Drug Delivery, Pharmaceutical Research, 1990, pp. 621-627, vol. 7, No. 6.

ISR and Written Opinion for PCT/EP2015/066457, dated Oct. 1, 2015.

ISR and Written Opinion for PCT/EP2015/066456, dated Oct. 1, 2015.

Third Party Observation for PCT/EP2015/066456, submitted Nov. 18, 2016.

\* cited by examiner

… (1)

ABUSE DETERRENT OPIOID/OPIOID-ANTAGONIST TRANSDERMAL PATCH

CROSS-REFERENCE TO RELATED APPLICATIONS

This application is a national stage entry under 35 USC § 371 of PCT International Application No. PCT/EP2015/066457, filed Jul. 17, 2015, and claims the benefit under 35 USC § 119(e) to U.S. Provisional Patent Application Nos. 62/187,473, filed Jul. 1, 2015, and 62/026,195, filed Jul. 18, 2014, the disclosures of which are expressly incorporated by reference in their entirety.

FIELD OF THE INVENTION

The present invention relates to a transdermal patch. More specifically, the present invention relates to an abuse deterrent transdermal patch for the transdermal administration of an opioid analgesic. The present invention also relates to processes for the preparation of the transdermal patches defined herein, as well as to the use of these patches for the treatment of pain.

BACKGROUND OF THE INVENTION

Opioid analgesics are widely used in the clinic to treat moderate to severe pain. However, despite their clinical efficacy, opioid analgesics do suffer from some major drawbacks. One major drawback is that prolonged opioid analgesic use can lead to dependence, which gives rise to withdrawal symptoms if the opioid analgesic treatment is stopped abruptly. This opioid dependence can make opioid analgesics very addictive and prone to abuse. In addition, opioid analgesics are also well known for their ability to produce a feeling of euphoria, motivating some to use opioids recreationally.

The prevalence of opioid analgesic abuse is a major problem and the Food and Drug Administration (FDA) in the United States has initiated a program to encourage manufacturers of extended release and transdermal opioid formulations to consider innovative strategies to reduce the risk of abuse, and thereby encourage safe opioid use.

The transdermal delivery of opioid analgesics is a convenient and effective way to deliver opioid analgesics. However, there remains a need for improved approaches for the transdermal delivery of opioid analgesics. In addition, there is a need for novel abuse-deterrent transdermal patches which prevent, or substantially reduce, the risk of opioid abuse.

Aspects of the invention were devised with the foregoing in mind.

SUMMARY OF THE INVENTION

In a first aspect, the present invention provides a transdermal patch comprising a multilaminate, said multilaminate comprising:
 (i) a first layer comprising an opioid analgesic compound, or a pharmaceutically acceptable salt thereof, and a pharmaceutically acceptable pressure sensitive adhesive;
 (ii) a second layer comprising an opioid antagonist, or a pharmaceutically acceptable salt thereof, and a pharmaceutically acceptable adhesive; and
 (iii) a barrier layer disposed between the first and second layers, and wherein the barrier layer substantially prevents the opioid antagonist diffusing from the second layer to the first layer during use;
wherein a proportion of the opioid antagonist in the second layer is present in the form of a pharmaceutically acceptable salt and a proportion of the opioid antagonist is present in a non-salt form (e.g. as a free base).

In a second aspect, the present invention provides a transdermal patch comprising a multilaminate, said multilaminate comprising:
 (i) a first layer comprising an opioid analgesic compound, or a pharmaceutically acceptable salt thereof, and a pharmaceutically acceptable pressure sensitive adhesive;
 (ii) a second layer comprising an opioid antagonist, or a pharmaceutically acceptable salt thereof, and a pharmaceutically acceptable adhesive; and
 (iii) a barrier layer disposed between the first and second layers, and wherein the barrier layer substantially prevents the opioid antagonist diffusing from the second layer to the first layer during use;
wherein said barrier layer comprises a material selected from the group consisting of polyethylene, ethylene vinyl acetate, polypropylene, polyurethane, polyvinyl acetate, polyvinylidene chloride, polyester, polyethylene terephthalate, polybutylene terephthalate, rayon (synthetic textile fibres produced by forcing cellulose through fine spinnerets and solidifying the resultant filaments), wood pulp, and spun-laced polyester.

The transdermal patches of the present invention are abuse-deterrent patches. The barrier membrane serves to prevent, or substantially prevent, the opioid antagonist present in the second layer from permeating through to the first layer during normal use of the patch. As a consequence, little or no opioid antagonist permeates into the skin of a patient during normal use. If the patch is misused, however, for example by an individual wishing to extract the opioid analgesic from the patch by immersing it in certain solvents, such as water, ethanol or acetone, or by chewing the patch, then the opioid antagonist present in the second layer will be released in an amount sufficient to antagonise some or all of the effects of the opioid analgesic that is extracted. This means that the extracted opioid analgesic will not exhibit the pharmacological effects expected.

In order to effectively antagonise the effects of the opioid analgesic released from the transdermal patch in certain solvents, it is necessary for the ration of opioid analgesic to opioid antagonist to be within a certain range. The range required will depend on the particular opioid analgesic and antagonist used. Typically, the transdermal patches of the present invention release the opioid antagonist at a ratio of 60:1 to 1:60 (opioid analgesic : opioid antagonist) when the patch is immersed in water, acetone, ethanol or phosphate buffer (e.g. at a pH of 6-7) for a period of greater than 30 seconds, or greater than 1 minute, or greater than 2 minutes.

Suitably, the transdermal patches of the present invention release the opioid antagonist at a ratio of 4:1 to 1:4 (opioid analgesic : opioid antagonist) when the patch is immersed in water, acetone, ethanol or phosphate buffer (e.g. at a pH of 6-7) for a period of greater than 30 seconds, or greater than 1 minute, or greater than 2 minutes.

More suitably, the transdermal patches of the present invention release the opioid antagonist at a ratio of 4:1 to 1:1 (opioid analgesic : opioid antagonist) when the patch is immersed in water, acetone, ethanol or phosphate buffer (e.g. at a pH of 6-7) for a period of greater than 30 seconds, or greater than 1 minute, or greater than 2 minutes.

In a third aspect, the present invention provides a transdermal patch comprising only a first layer as defined herein. Suitably, the opioid analgesic present in said first layer is oxymorphone, or a pharmaceutically acceptable salt thereof.

In another aspect, the present invention provides a transdermal patch as herein defined for use as a medicament or for use in therapy.

In another aspect, the present invention provides a transdermal patch as herein defined for use in the treatment of pain.

In another aspect, the present invention provides a method of treating pain said method comprising applying a transdermal patch as herein defined. In another aspect, the present invention provides a method of preparing a transdermal patch as defined herein. Suitably, said method comprises mixing the components of the first and/or second layers defined herein respectively and wet casting to form the first and second layers defined herein; and assembling the multilaminate by placing a barrier membrane as defined herein between the first and second layers.

DETAILED DESCRIPTION OF THE INVENTION

Transdermal Patch of the First Aspect of the Invention

As indicated above, in a first aspect, the present invention provides a transdermal patch comprising a multilaminate, said multilaminate comprising:
(i) a first layer comprising an opioid analgesic compound, or a pharmaceutically acceptable salt thereof, and a pharmaceutically acceptable pressure sensitive adhesive;
(ii) a second layer comprising an opioid antagonist, or a pharmaceutically acceptable salt thereof, and a pharmaceutically acceptable adhesive;
(iii) a barrier layer disposed between the first and second layers, and wherein the barrier layer substantially prevents the opioid antagonist diffusing from the second layer to the first layer during use;
and wherein a proportion of the opioid antagonist in the second layer is present in the form of a pharmaceutically acceptable salt and a proportion of the opioid antagonist is present in a non-salt form (e.g. as a free base).

The first layer has a first surface that contacts the barrier membrane and a second opposing surface that contacts the skin during use. The opioid analgesic present in the first layer diffuses or permeates into the skin over time to provide the desired analgesic effect.

Similarly, the second layer has a first surface which contacts the barrier membrane and a second opposing surface.

The barrier membrane prevents or substantially prevents the opioid antagonist present in the second layer from permeating through to the first layer during normal use of the patch. As a consequence, little or no opioid antagonist permeates into the skin of a patient during normal use. If the patch is misused, however, for example by an individual wishing to extract the opioid analgesic from the patch using certain solvents such as water, ethanol or acetone, or by chewing the patch, then the opioid antagonist present in the second layer will be released to antagonise the effects of the opioid analgesic, thereby preventing the subsequent misuse of the extract opioid analgesic.

The transdermal patch suitably further comprises a backing membrane that extends over the second layer (i.e. over the second surface of the second layer). The second surface of the first layer is suitably covered with a peelable release liner that extends across the entire second surface of the first layer, but which can be removed to expose the second surface of the first layer prior to application of the patch to the skin.

Backing Membranes

Suitable backing membranes may be occlusive or non-occlusive. Where a non-occlusive backing membrane is used, it is desirable to use a fully occlusive container or closure system to prevent degradation of the cast pharmaceutical formulation layer prior to use. The backing membrane may be of any thickness, but is suitably between about 10 to 260 µm thick. Suitable materials include, but are not limited to, synthetic polymers including, for example, polyesters, polycarbonates, polyimides, polyethylene, poly(ethylene terphthalate), polypropylene, polyurethanes and polyvinylchlorides. The backing membrane may also be a laminate comprising additional layers that may include vapour deposited metal, such as aluminium, additional synthetic polymers, and other materials, to enable a heat seal, such as EVA copolymer. Suitably, the backing membrane comprises occlusive Scotchpak 9730® obtainable from 3M.

Release Liner

The release liner is typically disposed on an opposite surface of the multi-laminate (i.e. the second surface of the first layer) to the backing membrane and provides a removable protective or impermeable layer, usually but not necessarily rendered non-stick so as to not adhere to the first layer. The release liner serves to protect the first layer during storage and transit, and is intended to be removed prior to application to the skin. The release liner may be formed from the same materials used for the backing membrane, but may be formed from metal foils, Mylar®, polyethylene terephthalate, siliconized polyester, fumed silica in silicone rubber, polytretrafluoroethylene, cellophane, siliconized paper, aluminized paper, polyvinyl chloride film, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, and polypropylene.

Suitably, the release liner is an occlusive or semi-occlusive backing film being compatible with the pharmaceutically-acceptable adhesive present in the pharmaceutical formulation layer.

Suitably, the release liner may be selected from Scotchpak 9741®, Scotchpak 1022®, Scotchpak 9742®, Scotchpak 9744®, Scotchpak 9748® and Scotchpak 9755®, all of which are obtainable from 3M and comprise fluoropolymers coated onto polypropylene or polyester film. Other suitable release liners made by other manufacturers may also be used. The release liner may be of any thickness known in the art. Suitably the release liner has a thickness of about 0.01 mm to about 2 mm.

In one embodiment, the release liner is Scotchpak 9741®. In another embodiment, the release liner is Scotchpak 1022®.

The container or closure system may be made from a range of materials suitable for protecting the packaged transdermal patch from moisture and light.

The First Layer

In one embodiment, the first layer has a thickness of 0.1-100 mil, more suitably, 1-50 mil, even more suitably 2-20 mil, and most suitably 5-20 mil.

Opioid Analgesic

The first layer of the transdermal patches of the present invention comprise an opioid analgesic. Any suitable opioid analgesic may be used.

The opioid analgesic can be selected from the group comprising alfentanil, allylprodine, alphaprodine, anileridine, benzylmorphine, bezitramide, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levomethadyl, levophenacylmorphan, lofentanil, meperidine, metazocine, methadone, metopon, morphine, myrophine, narceine, nicomorphine, norlevorphanol, normethadone, normorphine, norpipanone, opium, oxycodone, oxymorphone, papaveretum, phenadoxone, phenomorphan, phenazocine, phenoperidine, piminodine, piritramide, propheptazine, promedol, properidine, propoxyphene, sufentanil, tilidine, tramadol, buprenorphine, butorphanol, dezocine, meptazinol, nalbuphine, nalorphine, pentazocine, tapentadol and salts of the foregoing. In another embodiment, the composition comprises pharmaceutically acceptable prodrugs of the opioid analgesic.

In an embodiment, the opioid analgesic is selected from morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine and buprenorphine, fentanyl, pethidine, levorphanol, methadone, tramadol, tapentadol and dextropropoxyphene.

In a further embodiment, the opioid analgesic is selected from buprenorphine, fentanyl, hydromorphone, oxycodone, tapentadol or oxymorphone, or a pharmaceutically acceptable salt thereof.

Any suitable opioid containing transdermal formulation may be used to form the first layer in the compositions of the present invention. Examples of suitable first layers for inclusion in the transdermal patches of the present invention include the fentanyl containing transdermal formulations described in EP 1381352 B1, U.S. Pat. Nos. 6,139,866, 5,985,317, 5,762,952 and 5,474,783, and tapentadol-containing transdermal formulations described in WO 2014012653, the entire contents of which are incorporated herein by reference.

In a particular embodiment, the opioid analgesic is oxymorphone, or a pharmaceutically acceptable salt thereof.

The amount of opioid analgesic present in the first layer of the patches of the present invention will depend on how soluble it is in the pharmaceutically-acceptable adhesive and excipients present in this layer and how much of the opioid is required in order to achieve the desired therapeutic effect. Typically, the opioid analgesic will be present at an amount of 1-10% w/w in the first layer.

In one embodiment, the amount of opioid analgesic present is 3-10% w/w in the first layer.

Suitably, the amount of opioid analgesic present is 4-7% w/w, and even more suitably 4-6% w/w, in the first layer.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Although the opioid analgesic may be present in the form of a salt, a person skilled in the art will appreciate that the opioid analgesic needs to be in a form that has a suitable lipophilic/hydrophilic balance so as to enable good permeation through the skin. In some embodiments of the invention, the opioid analgesic is present in a non-salt form, i.e. as a free base or acid.

Pharmaceutically-acceptable Adhesive

The pharmaceutically-acceptable adhesive present in the first layer is selected both in terms of its ability to solubilise the opioid analgesic, and its adhesive tack and peel properties.

In one embodiment, the adhesive has an opioid analgesic solubility in excess of 2.5% w/w at room temperature.

Typically, the total amount of adhesive will constitute between 58 and 99% w/w of the first layer.

Any suitable adhesive material or combination of adhesive materials may be used. Such materials are suitably pressure sensitive adhesives.

Examples of suitable pressure sensitive adhesives include polymer and copolymers of polyacrylates, polysiloxanes, polyisobutylene, polyisoprene, polybutadiene, ethylene-vinyl acetate and styrenic block polymers, such as styrene-isoprene-styrene block copolymer, styrene-butadiene-styrene copolymer, styrene-ethylenebutene-styrene copolymers, styrene-ethylene/propylene-styrene copolymers and di-block analogs thereof. Examples of polyacrylates include, but are not limited to, acrylic acids, alkyl acrylates and methacrylates; for example, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, vinylacetate/ethylene acrylate and the like. Additional examples of appropriate acrylic adhesives suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Other useful pressure sensitive adhesives (PSA) can include mixtures of different polymers or mixtures of polymers such as synthetic rubber polyisobutylene (PIB), The PIB adhesives normally include a tackifier such as polybutene oil and resins such as the ESCOREZ® resins available from Exxon Chemical. Other useful rubber-based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof. Polyisobutylene polymers are available commercially under the trademark name VISTANEX® from Exxon Chemical.

Silicone-based pressure sensitive adhesives are also suitable for use in additional embodiments described herein. Suitable silicone-based pressure-sensitive adhesives can include those described in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989), incorporated by reference in its entirety. Other useful silicone-based pressure sensitive adhesives are described in the following U.S. Pat. Nos. 4,591,622; 4,584,355; 4,585,836; and 4,655,767 which are hereby incorporated by reference in their entirety. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich. The commercially available silicones are sold under the trademark of BIO-PSA such as Bio-PSA 7-4102, 7-4202, 7-4302, 7-4101, 7-4201, 7-4301, 7-4303, 7-4503, 7-4603 by Dow Corning Cooperation. In one embodiment, amine-compatible Bio-PSA silicone adhesives are preferred. In a further embodiment, the preferred amine-compatible Bio-PSA silicone adhesive 7-4202 was employed in combination with acrylic adhesive such as Duro-tak 87-9301 manufactured by National Starch and Chemical Company.

In one embodiment a pressure sensitive adhesive is optionally used to assist in affixing a patch containing an opioid to be transdermally delivered to the subject. In a further embodiment, the pressure sensitive adhesive is present in a total amount by weight between about 58% and about 99%; between about 60% and about 95% and between about 70% and about 90% of the first layer. In a further embodiment the pressure sensitive adhesive layer is a mixture of two or more pressure sensitive adhesives.

In an embodiment, the adhesive is selected from acrylate/polyacrylate materials, rubbers and silicones.

In a further embodiment, the adhesive is selected from acrylate/polyacrylate materials and silicones.

In yet a further embodiment, the adhesive is mixture of an acrylate/polyacrylate material and a silicone material.

Suitably, the silicone adhesive comprises a composition of a silicone adhesive in a suitable solvent, for example ethyl acetate and/or hexane. As indicated above, examples of such adhesives includes those that are commercial available from Dow Corning® under the BIOPSA® product range. These adhesives are compatible with amine containing drugs and are formed by a condensation reaction of silanol end-blocked polydimethylsiloxane (PDMS) with a silicate resin, and the residual silanol functionality is then capped with trimethylsiloxy groups to yield the chemically stable amine-compatible adhesives.

Particular examples of suitable silicone adhesives include BIO-PSA® 7-4502, 7-4302 and 7-4202 or mixtures thereof.

Suitably the silicone based adhesive represents 60-98% w/w of the first layer. More suitably, the silicone based adhesive represents 60-90% w/w of the first layer. Even more suitably, the silicone based adhesive represents 60-80% w/w of the first layer. Most suitably, the silicone based adhesive represents 70-80% w/w of the first layer.

Suitably the acrylate or polyacrylate material is an acrylate copolymer and/or an acrylate-vinyl acetate, such as Duro-Tak 87-2677®, Duro-Tak 87-900A®, Duro-Tak 87-2074®, Duro-Tak 87-2054®, Duro-Tak 87-2052®, Duro-Tak 87-2196®, Duro-Tak 9301®, Duro-Tak 2054®, Duro-Tak 606A®, and/or Duro-Tak 202A obtainable from Henkel.

In a particular embodiment, the acrylate or polyacrylate material is selected from Duro-Tak 9301®, Duro-Tak 2054®, Duro-Tak 606A®, and/or Duro-Tak 202A®.

In a further embodiment, the acrylate or polyacrylate material is Duro-Tak 9301®.

The amount of the acrylate or polyacrylate material present may be within the range of 0 to 98% w/w of the first layer.

Suitably, the acrylate or polyacrylate material is present in addition to the silicone adhesive at the amounts specified above. In such embodiments, the amount of the acrylate or polyacrylate material present is within the range of 1-15% w/w of the first layer. In further embodiments, where the acrylate or polyacrylate material is present in addition to the silicone adhesive at the amounts specified above, the amount of the acrylate or polyacrylate material present is within the range of 3-12% w/w of the first layer, or 5 to 12% w/w of the first layer.

In one embodiment, a suitable volatile solvent is added to the adhesive to reduce viscosity and aid solvation. Suitable solvents may include, but are not limited to, isopropyl alcohol, methanol, ethanol and ethyl acetate.

Penetration Enhancer

Suitably, the first layer further comprises a penetration enhancer.

The composition may comprise one or more penetration enhancers for transdermal drug delivery. Examples of penetration enhancers include C8-C22 fatty acids such as isostearic acid, octanoic acid, myristic acid and oleic acid; C8-C22 fatty alcohols such as oleyl alcohol and lauryl alcohol; lower alkyl esters of C8-C22 fatty acids such as ethyl oleate, isopropyl myristate (IPM), butyl stearate, and methyl laurate; di(lower)alkyl esters of C6-C22 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxy) ethanol (transcutol); diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes.

In a particular embodiment, the penetration enhancer is oleic acid, myristic acid or 1:1 oleic acid:oleyl alcohol.

In an embodiment, the first layer comprises one penetration enhancer. In another embodiment, the composition comprises two penetration enhancers.

The penetration enhancer is present in an amount sufficient to provide the desired physical properties and skin penetration profile for the composition.

For example, one or more pharmaceutically acceptable penetration enhancers can be present in a total amount by weight of 0.1-15% w/w of the first layer. In an embodiment, one or more pharmaceutically acceptable penetration enhancers are present in a total amount by weight between 2% and 12% w/w of the first layer, or between 5% and 12% w/w, or between 7% and 11% w/w.

Hydrophilic Materials

In certain embodiments, the use of hydrophilic materials in the first layer may aid the skin absorption of the opioid analgesic or the solubility of the drug in the adhesive. Suitably, the hydrophilic material, and the quantities in which it is added, should be non-toxic, non-irritating, non-allergenic, and compatible with the opioid analgesic and the other excipients herein described.

In one embodiment, the hydrophilic material will have a hydrophilic-lipophilic balance (HLB) of greater than 7. Examples of hydrophilic materials suitable for inclusion into the pharmaceutical formulation of the present invention include, but are not limited to, propylene glycol, dipropylene glycol, glycerol, polyethylene glycol, short chain water soluble esters of citric acid, acetic acid, hexylene glycol and alcohols, including diols and polyols.

The amount of hydrophilic material present is 0-20% w/w.

Suitably, when used, the hydrophilic material is present in the first layer in an amount of between 1.0% w/w and 20% w/w.

Suitably, the hydrophilic material, when present, is in an amount of between 0.5 and 10% w/w, and more suitably between 1 and 8% w/w.

Suitably, the hydrophilic material is propylene glycol or dipropylene glycol.

In an embodiment, the hydrophilic material is included in the first layer as part of a mixture including the opioid analgesic, the pharmaceutically acceptable adhesive and a penetration enhancer.

Particular Embodiments of the First Layer

The following represent particular embodiments of the first layer:

| 1.1 | Opioid analgesic (e.g. oxymorphone) | 1-10% w/w |
| --- | --- | --- |
| | Pharmaceutically acceptable adhesive | 58-98% w/w |
| | Penetration enhancer (e.g oleic acid, myristic acid, and/or oleyl alcohol) | 0.1-15% w/w |
| | Hydrophilic material (e.g. propylene glycol) | 0-20% w/w |
| 1.2 | Opioid analgesic (e.g. oxymorphone) | 3-10% w/w |
| | Acrylate/polyacrylate adhesive (e.g. BIO-PSA 7-4502, 7-4302 and 7-4202) | 60-80% w/w |
| | Silicone adhesive (e.g. Duro-Tak 9301 ®) | 0-15% w/w |
| | Penetration enhancer (e.g oleic acid, myristic acid and/or oleyl alcohol) | 2-12% w/w |
| | Hydrophilic material (e.g. propylene glycol) | 0-10% w/w |
| 1.3 | Opioid analgesic (e.g. oxymorphone) | 4-6% w/w |
| | Acrylate/polyacrylate adhesive (e.g. BIO-PSA 7-4502, 7-4302 and 7-4202) | 70-80% w/w |
| | Silicone adhesive (e.g. Duro-Tak 9301 ®) | 0-12% w/w |
| | Penetration enhancer (e.g oleic acid, myristic acid, and/or oleyl alcohol) | 5-12% w/w |
| | Hydrophilic material (e.g. propylene glycol) | 0-8% w/w |
| 1.4 | Opioid analgesic (e.g. oxymorphone) | 4-6% w/w |
| | Acrylate/polyacrylate adhesive (e.g. BIO-PSA 7-4502, 7-4302 and 7-4202) | 70-80% w/w |
| | Silicone adhesive (e.g. Duro-Tak 9301 ®) | 0-12% w/w |
| | Penetration enhancer (e.g oleic acid, myristic acid and/or oleyl alcohol) | 5-12% w/w |
| | Hydrophilic material (e.g. propylene glycol) | 0-8% w/w |

Particular examples of the first layer are provided in Example 1 herein.

The Second Layer

The thickness of the second may be 0.1-100 mil, more suitably 10-75 mil, and even more suitably 15-60 mil.

Opioid Antagonist

Suitably, the opioid antagonist is present in an amount of 1-20% w/w, or 8-12% w/w, and even more suitably, 9-11% w/w in the second layer.

The opioid antagonist is suitably selected from the group consisting of: naltrexone ("NTX"), 6-beta-naltrexol, nalbuphine, nalmefene, naloxone ("NLX"), cyclazocine, levallorphan, cyclorphan, oxilorphan and pharmaceutically acceptable salts and prodrugs thereof.

Suitably, the opioid antagonist is naltrexone ("NTX"), naloxone ("NLX") or nalmefene.

In the first aspect of the present invention, a proportion of the opioid antagonist is present in the form of a pharmaceutically acceptable salt and the remainder is present in a non-salt (e.g. free base) form.

The amount of the salt form of the opioid antagonist present may be 5-95% w/w, more suitably 15 to 80% w/w, even more suitably 30-70% w/w and most suitably 45-55% w/w of the total opioid antagonist present in the second layer (and the balance is the non-salt (e.g. free base) form).

The use of just the non-salt form of the antagonist, e.g. the free base of naltroxone or naloxone, has been found to result in some migration of the antagonist into first layer during use with certain barrier layers. Conversely, the use of just the salt form can prevent this migration during use, but then does not give the desired release rate of antagonist with the opioid when the patch is exposed to solvents such as water, phosphate buffered saline, ethanol and acetone.

The use of both the salt and non-salt forms together enables a balance between the migration through to the first layer during use and the achieving the required release ratio of antagonist to opioid analgesic when the patch is subject to abuse. This enables a larger number of barrier membranes to be used.

The amount of opioid antagonist present in the second layer of the patches of the present invention will depend on how soluble it is in the pharmaceutically-acceptable adhesive and any other excipients present in this layer, and how much of the opioid antagonist is required relative to the opioid agonist in order to achieve the desired abuse deterrent effect. Typically, the opioid antagonist will be present at an amount of 2-15% w/w in the second layer.

In one embodiment, the opioid antagonist is present in an amount of 5-12% w/w in the second layer.

Pharmaceutically-acceptable Adhesive

The pharmaceutically-acceptable adhesive present in the second layer is selected both in terms of its ability to solubilise the opioid antagonist and its adhesive tack properties.

In one embodiment, the adhesive has an opioid antagonist solubility in excess of 2.5% w/w at room temperature.

Typically, the amount of adhesive is between 58 and 98% w/w of the second layer, and more suitably 60-80% w/w, and even more suitably 60-70% w/w.

Any suitable adhesive material or combination of adhesive materials as defined above in relation to the first layer may be used.

Suitably, an acrylate or polyacrylate adhesive material and/or a silicone adhesive as defiend in relation to the first layer represents 50-98% w/w of the second layer, and more suitably 55-75% w/w, and even more suitably 60-70% w/w of the second layer.

Additional adhesives, such as, for example, polyvinylpyrollidinone (e.g. polyvinylpyrollidone K30) may also be present, for example in amount of between 0.5 to 15% w/w of the second layer, or 1 to 6% w/w, or 2 to 5% w/w.

In one embodiment, a suitable volatile solvent is added to the adhesive to reduce viscosity and aid solvation. Suitable solvents may include, but are not limited to, isopropyl alcohol, methanol, ethanol and ethyl acetate.

Cellulose Components

The second layer may further comprise 0-30% w/w of cellulose components, for example ethyl cellulose, hydroxypropyl cellulose or a mixture thereof. Suitably, 0-25% w/w of such components may be present.

In an embodiment, the second layer comprises 5 to 25% w/w of cellulose components.

In a further embodiment, the second layer comprises 5 to 25% w/w of an ethyl cellulose/hydroxypropyl cellulose mixture (e.g. at a ratio of 0.5-10:1 of ethyl cellulose: hydroxypropyl cellulose).

Hydrophilic Materials

The second layer may optionally comprise a hydrophilic material as defined hereinbefore in relation to the first layer.

The amount of hydrophilic material present in the second layer is 0-20% w/w.

Suitably, when used, the hydrophilic material is present in the second layer in an amount of between 1.0% w/w and 10% w/w.

Suitably, the hydrophilic material, when present, is in an amount of between 0.5 and 10% w/w, and more suitably between 1 and 8% w/w.

Suitably, the hydrophilic material is propylene glycol or dipropylene glycol.

Particular Embodiments of the Second Layer

The following represent particular embodiments of the second layer:

| | | |
|---|---|---|
| 2.1 | Opioid antagonist | 1-20% w/w |
| | Pharmaceutically acceptable adhesive | 58-98% w/w |
| | Cellulose components (e.g ethyl cellulose and/or hydroxypropyl cellulose) | 0-25% w/w |
| | Hydrophilic material (e.g. propylene glycol or dipropylene glycol) | 0-20% w/w |
| 2.2 | Opioid antagonist | 8-12% w/w |
| | Pharmaceutically acceptable adhesive (e.g. BIO-PSA 7-4302 and/or Duro-Tak 9301) | 60-80% w/w |
| | Cellulose components (e.g ethyl cellulose and/or hydroxypropyl cellulose) | 0-20% w/w |
| | Hydrophilic material (e.g. propylene glycol or dipropylene glycol) | 0-10% w/w |
| 2.3 | Opioid antagonist | 8-12% w/w |
| | Pharmaceutically acceptable adhesive (e.g. BIO-PSA 7-4302 and/or Duro-Tak 9301) | 60-70% w/w |
| | Cellulose components (e.g ethyl cellulose and/or hydroxypropyl cellulose) | 0-20% w/w |
| | Hydrophilic material (e.g. propylene glycol or dipropylene glycol) | 0-10% w/w |

Particular examples of the second layer are provided in Example 2 herein.

Additional Optional Excipients in the First and Second Layers:

In addition to the opioid analgesic, the adhesive and optionally the penetration enhancer, the first layer may optionally comprise one or more additional excipients, for example, hydrophilic polymers, wetting agents, emollients, antioxidants or emulsifying agents.

The first and second layers described herein optionally comprise one or more pharmaceutically acceptable wetting agents as excipients. Examples of surfactants that can be used as wetting agents in compositions of the disclosure include quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10, and octoxynol 9; poloxamers (polyoxyethylene and polyoxypropylene block copolymers); polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether; polyoxyethylene fatty acid esters, for example polyoxyethylene (40) stearate; polyoxyethylene sorbitan esters, for example polysorbate 20 and polysorbate 80 (e.g., Tween™ 80 of ICI); propylene glycol fatty acid esters, for example propylene glycol laurate (e.g., Lauroglycol™ of Gattefosse); sodium lauryl sulfate, fatty acids and salts thereof, for example oleic acid, sodium oleate and triethanolamine oleate; glyceryl fatty acid esters, for example glyceryl monostearate; sorbitan esters, for example sorbitan monolaurate, sorbitan monooleate, sorbitan monopalmitate and sorbitan monostearate; tyloxapol; and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25-10% w/w of the first layer.

The first and second layers described herein optionally comprise one or more pharmaceutically acceptable lubricants (including anti-adherents and/or glidants) as excipients. Suitable lubricants include, either individually or in combination, glyceryl behenate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. Illustratively, one or more pharmaceutically acceptable lubricants may be present in a total amount by weight of 0.1% -10.0%.

In another embodiment, the first and second layers described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate (IPM), isopropyl palmitate, lecithin, allyl caproate, althea officinalis extract, arachidyl alcohol, argobase EUC, butylene glycol, dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soybean, octyl palmitate, caprylic/capric triglyceride and glyceryl cocoate.

An emollient, if present, is present in the first and second layers described herein in an amount of 1% -30% w/w, or 3% -25% w/w, or 5-15% w/w.

In one embodiment, the first and second layers described herein comprise an antioxidant. Illustrative antioxidants include citric acid, butylated hydroxytoluene (BHT), ascorbic acid, glutathione, retinol, alpha-tocopherol, beta-carotene, alpha-carotene, ubiquinone, butylated hydroxyanisole, ethylenediaminetetraacetic acid, selenium, zinc, lignan, uric acid, lipoic acid, and N-acetylcysteine. An antioxidant, if present, is present in the first and second layers described herein in the amount of less than about 1% by weight.

In one embodiment, the first and second layers described herein comprise an antimicrobial preservative. Illustrative anti-microbial preservatives include acids, including but not limited to benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. The anti-microbial preservative, if present, is present in an amount of about 0.1% to 5% w/w, or 0.2% to 3% w/w, or 0.3% to 2% w/w.

The first and second layers described herein optionally comprise one or more emulsifying agents. The term "emulsifying agent" refers to an agent capable of lowering surface tension between a non-polar and polar phase and includes compounds defined elsewhere as "self-emulsifying" agents. Suitable emulsifying agents can come from any class of pharmaceutically acceptable emulsifying agents including carbohydrates, proteins, high molecular weight alcohols, wetting agents, waxes and finely divided solids. The optional emulsifying agent may be present in the first and second layers in a total amount of 1-25% w/w, or 1-20% w/w, or 1-15% w/w, or 1-10% w/w of the first and second layers.

In another embodiment, propylene glycol or dipropylene glycol is present in a composition in an amount of 1-20% by weight of the first and second layers.

The first and second layers described herein may optionally comprise one or more alcohols. In a further embodiment, the alcohol is a lower alcohol. As used herein, the term "lower alcohol," alone or in combination, means a straight-chain or branched-chain alcohol moiety containing one to six carbon atoms. In one embodiment, the lower alcohol contains one to four carbon atoms, and in another embodiment the lower alcohol contains two or three carbon atoms. Examples of such alcohol moieties include ethanol, ethanol USP (i.e., 95% v/v), n-propanol, isopropanol, n-butanol, isobutanol, sec-butanol, and tert-butanol. As used herein, the term "ethanol" refers to $C_2H_5OH$. It may be used as dehydrated alcohol USP, alcohol USP or in any common form including in combination with various amounts of water. If present, the alcohol is present in an amount sufficient to form a composition which is suitable for contact with a mammal.

In a further embodiment, the pharmaceutical composition is substantially free of water. In yet a further embodiment, the pharmaceutical composition is anhydrous.

Barrier Layer

The barrier layer is disposed between the first and second layers and functions to substantially prevent the opioid antagonist diffusing from the second layer to the first layer during normal use of the patch. The barrier layer also enables the release of the antagonist from the second layer at a rate sufficient to inhibit the abuse potential of the opioid analgesic when the patch is tampered with (by, for example, chewing the patch or immersing it in a solvent such as water, ethanol or acetone).

As indicated above, the use of a salt and non-salt form of the opioid antagonist enables a larger number of barrier membranes to be used.

In the first aspect of the present invention, any suitable barrier membrane may used. Examples include membranes made from polyethylene, ethylene vinyl acetate, polypropylene (e.g. ultra high density polyethylene), polyurethane, polyvinyl acetate, polyvinylidene chloride, polyester, polyethylene terephthalate, polybutylene terephthalate, rayon (synthetic textile fibres produced by forcing cellulose through fine spinnerets and solidifying the resultant filaments), wood pulp, and spun-laced polyester.

Preferred membranes include membranes made from polyethylene and ethylene vinyl acetate. In particular, Solupor microporous ultra high density polyethylene (UHDPE) materials and films (Solupor® manufactured by DSM Desotech, Denmark) are particularly effective at inhibiting the permeation of the opioid antagonist from the second layer to the first layer during use (redgardless of whether or not it is in a non-salt or salt form), yet enabling the antagonist to be released in an abuse inhibiting ratio with the opioid analgesic when the patech is tampered with. Ethylene vinyl acetate (EVA) membranes made by 3M under the trade name CoTran are also viable alternatives.

Transdermal Patch of the Second Aspect of the Invention

In a second aspect, the present invention provides a transdermal patch comprising a multilaminate, said multilaminate comprising:

(i) a first layer comprising an opioid analgesic compound as defined hereinbefore, or a pharmaceutically acceptable salt thereof, and a pharmaceutically acceptable pressure sensitive adhesive;

(ii) a second layer comprising an opioid antagonist, or a pharmaceutically acceptable salt thereof, and a pharmaceutically acceptable adhesive as defined hereinbefore; and (iii) a barrier layer disposed between the first and second layers, and wherein the barrier layer substantially prevents the opioid antagonist diffusing from the second layer to the first layer during use;

wherein said barrier layer comprises a material selected from the group consisting of polyethylene, ethylene vinyl acetate, polypropylene, polyurethane, polyvinyl acetate, polyvinylidene chloride, polyester, polyethylene terephthalate, polybutylene terephthalate, rayon (synthetic textile fibres produced by forcing cellulose through fine spinnerets and solidifying the resultant filaments), wood pulp, and spun-laced polyester.

The patches of the second aspect of the present invention may be used with the antagonist in the second layer either entirely in a non-salt (e.g. free base) or salt form or in a mixture of the free base and salt forms.

Suitably, in the patches of the second aspect of the present invention, the antagonist in the second layer either entirely in a non-salt (e.g. free base) form or in a mixture of the free base and salt forms as defined above for the first aspect of the invention.

Preferred membranes of the second aspect include membranes made from polyethylene and ethylene vinyl acetate. In particular, Solupor microporous ultra high density polyethylene (UHDPE) materials and films (Solupor manufactured by DSM Desotech, Denmark) are particularly effective at inhibiting the permeation of the opioid antagonist from the second layer to the first layer during use (redgardless of whether or not it is in a non-salt or salt form), yet enabling the antagonist to be released in an abuse inhibiting ratio with the opioid analgesic when the patech is tampered with. Ethylene vinyl acetate (EVA) membranes made by 3M under the trade name CoTran are also viable alternatives.

Combination Patches

In one embodiment, the first layer of the particles defined herein containing the opioid can also be combined with an optional second non-opioid pharmacologically active agent for the treatment of pain and/or polydrug abuse, including, for example, a cannabinoid (agonist, antagonist, or inverse agonist), bupropion, hydroxybupropion, nicotine, nornicotine, varenicline, doxepin, acetaminophen, aspirin, diclofenac or another non-steroidal anti-inflammatory drug.

Therapeutic Uses

The patches of the present invention may be used for the treatment of one or more medical conditions, such as opioid dependence, alcohol dependence, polydrug addiction, pain, cocaine addiction, eating disorders (e.g., binge eating) and treatment-resistant depression are described herein and comprise transdermally administering an opioid from an formulation as defined herein. In one embodiment, compositions described herein which are transdermally administrable include opioid analgesics such as oxymorphone and opioid antagonists, such as naltrexone and/or naloxone.

The compositions described herein are used in a "pharmacologically effective amount." This means that the rate and extent of absorption of the active by the subject is such that it results in a therapeutic level of the active in the subject over the period that such compound is to be used. Such delivery is dependent on a number of variables including the time period for which the individual dosage unit is to be used, the flux rate of the active from the composition into the subject, for example, buprenorphine or a buprenorphine prodrug, from the formulation, surface area of the application site, etc.

In another embodiment, a single dosage unit comprises a therapeutically effective amount or a therapeutically and/or prophylactically effective amount of an opioid analgesic such as oxymorphone. The term "therapeutically effective amount" or "therapeutically and/or prophylactically effective amount" as used herein refers to an amount of opioid that is sufficient to elicit the required or desired therapeutic and/or prophylactic response, as the particular treatment context may require. Single dosage unit as used herein includes individual patches. In one embodiment, a single dosage unit of any formulation comprises a therapeutically effective amount or a therapeutically and/or prophylactically effective amount of buprenorphine or a buprenorphine prodrug.

It will be understood that a therapeutically and/or prophylactically effective amount of an opioid for a subject is dependent inter alia on the body weight of the subject as well as other factors known to a person of ordinary skill in the art. A "subject" herein to which a therapeutic agent or composition thereof can be administered includes mammals such as a human of either sex and of any age, and also includes any nonhuman animal, particularly a domestic, farm or companion animal, illustratively, a cat, cow, pig, dog or a horse as well as laboratory animals such as guinea pigs and primates.

In one embodiment, compositions described herein are suitable for transdermal administration. In another embodiment, transdermally administrable compositions are adapted for administration to the abdomen, back, chest, legs, arms, scalp or other suitable skin surface.

The terms "treat", "treated", "treating" and "treatment" are to be broadly understood as referring to any response to, or anticipation of, a medical condition in a mammal, particularly a human, and includes but is not limited to: (i) inhibiting the medical condition, i.e., arresting, slowing or delaying the on-set, development or progression of the medical condition; or (ii) relieving the medical condition, i.e., causing regression of the medical condition.

In one embodiment, a therapeutically effective amount of an opioid, such as buprenorphine, is administered transdermally in an formulation as defined herein to treat a medical condition selected from the group consisting of: opioid dependence, alcohol dependence, polydrug addiction, pain, cocaine addiction, eating disorders (e.g., binge eating) and treatment-resistant depression.

Pain can include nociceptive pain, such as somatic pain and visceral pain, and non-nociceptive pain, such as neuropathic pain, sympathetic pain, psychogenic pain and idiopathic pain. Pain also includes chronic and acute pain. Non-limiting examples of pain or sources of pain include fibromyalgia, chronic back pain (both deep and superficial somatic pain), chronic pancreatitis, chronic acute hepatitis, gallstone, appendicitis, post-herpetic neuralgia, trigeminal neuralgia, phantom limb pain, diabetic neuropathy, carpal tunnel syndrome, sciatica, pudendal neuralgia, central pain syndrome, spinal cord injury, post-surgical pain, cancer, degenerative disk disease, osteoporosis, peripheral neuropathy, herpes zoster (shingles), lupus, reflex sympathetic dystrophy, headaches (migraines, tension and cluster), temporomandibular disorders, such as temporomandibular joint syndrome, myofacial pain and internal derangement of the joint and degenerative joint disease, such as osteoarthritis and rheumatoid arthritis.

Eating disorders can include anorexia nervosa, bulimia nervosa, binge eating disorder (BED), compulsive overeating, purging disorder, rumination, diabulimia, food maintenance, eating disorders not otherwise specified (EDNOS), pica, night eating syndrome and orthorexia nervosa.

In one embodiment, the pharmaceutical composition comprising an opioid, such as oxymorphone, is administered once daily to a subject in need thereof. In a further embodiment, the pharmaceutical composition comprising an opioid, such as oxymorphone, is administered twice daily to a subject in need thereof.

In another illustrative embodiment, a transdermal patch can be one which is capable of controlling the release of the opioid agonists or agonist-antagonists or prodrugs of the foregoing such that transdermal delivery of the active compound is substantially uniform and sustained over a period of about 6 hours, about 12 hours, about 24 hours, about 48 hours or about 7 days. Such transdermal patch which can be used in the practice of the methods described herein can take the form of an occlusive body having a backing layer. In practice, the occlusive body which includes the opioid agonists or agonist-antagonists or prodrugs of the foregoing is positioned on the subject's skin under conditions suitable for transdermally delivering the active compound to the subject Preparation of Pharmaceutical Formulations The transdermal patches of the present invention can be prepared using conventional techniques known in the art.

Transdermal Patches Comprising the First Layer Only

The first layer defined herein is suitably prepared by mixing all of the components together. The individual components may be mixed by simply adding all of the components at the same time into a mixing vessel and then mixing them all together (a "one-pot" mixture). Alternatively, the components may be added sequentially in two or more steps or stages.

Other experimental conditions required to prepare the formulations of the present invention, such as mixing times, mixing equipment, temperature control etc. can be readily determined by a person of ordinary skill in the art.

Further experimental details will also be evident from the accompanying Examples.

Once components have been mixed together the layers can be prepared by wet casting a desired thickness onto a suitable surface, e.g. a release liner. The layer can then be dried and stored ready for assembly.

Typically, the first layer is cast at a wet thickness of between about 240 µm to about 550 µm, to provide a dry thickness of between about 45 µm and about 95 µm, suitably between about 80 µm and about 85 µm. After casting, the layers are dried.

Suitably, the first layer is wet cast onto a release liner as defined herein (e.g. 3M Scotchpak 1022).

Transdermal Patches Comprising the First, Second and Barrier layer

The first and second layers defined herein are suitably prepared by mixing all of the components together. The individual components may be mixed by simply adding all of the components at the same time into a mixing vessel and then mixing them all together (a "one-pot" mixture). Alternatively, the components may be added sequentially in two or more steps or stages.

Other experimental conditions required to prepare the formulations of the present invention, such as mixing times, mixing equipment, temperature control etc. can be readily determined by a person of ordinary skill in the art.

Further experimental details will also be evident from the accompanying Examples.

Once components have been mixed together the layers can be prepared by wet casting a desired thickness onto a suitable surface, e.g. a release liner. The layer can then be dried and stored ready for assembly.

Typically, the first and second layers are cast at a wet thickness of between about 240 µm to about 550 µm, to provide a dry thickness of between about 45 µm and about 95 µm, suitably between about 80 µm and about 85 µm. After casting, the layers are dried.

The layers are assembled to form the multilaminate structures defined herein. Suitably, the first layer is wet cast onto a release liner as defined herein (e.g. 3M Scotchpak 1022). One surface of the first layer is therefore in contact with the release liner and the barrier membrane is applied to the opposing surface, followed by the second layer and a backing membrane to complete the assembly of the patch.

EXAMPLES

Examples of the invention will now be described, for the purpose of reference and illustration only, with reference to the accompanying figures, in which.

Materials and Procedures

Chemicals

Figure 1:
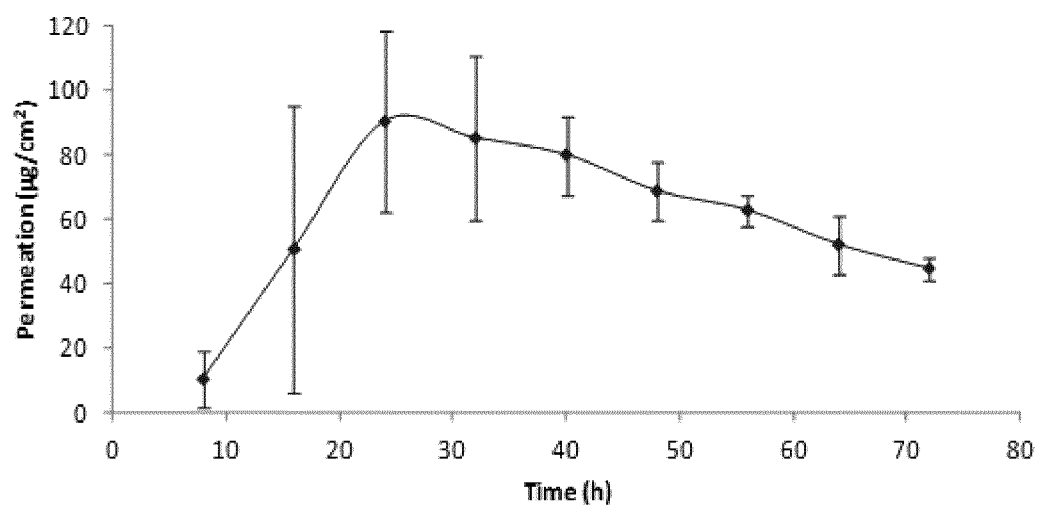
FIG. 1 shows the representative human skin permeation profile of oxymorphone formulation, OM-2014-01-011 (n=3)

The various chemicals used throughout these examples are as follows:

| Chemical | Manufacturer | Part # | CAS | Lot # |
|---|---|---|---|---|
| Oxymorphone hydrochloride, USP | Mallinckrodt Inc. | 079006 | 357-07-3 | 1304000913 |
| Potassium phosphate, monobasic | Fisher Scientific | BP362-500 | 7778-77-0 | 132450 |
| Potassium phosphate dibasic trihydrate | Acros Organics | AC20593-5000 | 16788-57-1 | A0331382 |
| Propylene glycol, USP | Spectrum Chemicals | PR130-500mL | 57-55-6 | 2BG0259 |
| Ethanol, 200 proof, USP | Sigma Aldrich | 493546-500mL | 64-17-5 | SHB04820V |
| Alcohol (ethyl alcohol) 190 proof USP | Spectrum | ET108 | 64-17-5, 7732-18-5 | 2CD0092 |
| Ethyl acetate, NF | Fisher Scientific | E124-20 | 141-78-6 | 134168 |
| Myristic acid myristyl ester | MP Biomedicals | 0215575591 | 3234-85-3 | 155755 |
| Oleic acid, NF | Spectrum Chemicals | OL103-1LTGL | 112-80-1 | |
| Myristic acid, reagent | Spectrum Chemicals | MY110-100GM | 544-63-8 | WV3017 |
| BIO-PSA AC7-4302 | Dow Corning | 3275205 | 238094-36-5, 141-78-6, 1330-20-7 | 0006099302 |
| BIO-PSA 7-4202 | Dow Corning | 000015563317 | 238094-36-5, 141-78-6, 1330-20-7 | 0006001327 |
| Duro-Tak ® 2054 | Henkel | 387-2054 | 200-661-7, 205-500-4, 203-624-3, 203-625-9 237-741-6, 203-806-2, 205-480-7 | 2Q939447717 |
| Duro-Tak ® 608A | Henkel | 1214080 | 142-82-5, 9003-27-4 | 20382-12 |
| Duro-Tak ® 4098 | Henkel | 1219326 | 141-78-6, 108-05-4 | OH31424641 |
| Duro-Tak ® 9301 | Henkel | 1428620 | 141-78-6 | OH14495473 |
| Duro-Tak ® 202A | Henkel | 87-202A | 141-78-6, 67-63-0, 67-56-1 | OH90213550 |
| Klucel ® EF PH | Hercules Incorporated | NA | 9004-64-2 | 99860 |
| Aqualon ® EC-N50 PH | Hercules Incorporated | NA | 9004-57-3 | 42118 |
| Polyvinylpyrrollidone (PVP-K30) | Spectrum Chemicals | P1454 | 9003-39-8 | XQ0602 |
| Polyvinylpyrrollidone vinyl acetate | Sigma Aldrich | 190845-250g | 25086-89-9 | MKBC1985 |
| Chloroform | JT Baker | 9182-01 | 67-66-3 | J02B18 |
| Sodium hydroxide | JT Baker | 3722-01 | 1310-73-2 | J20K52 |
| Sodium chloride | Fisher Scientific | M-11624 | 7647-14-5 | 102040 |
| Acetonitrile, HPLC grade | Fisher Scientific | A998-4 | 75-05-8 | 138059 |
| Methanol, HPLC grade | Fisher Scientific | A452-4 | 67-56-1 | 124875 |

Supplies

Supplies used throughout these examples are as follows:
1) XBridge® C18 column; 5 µm, 4.6×250 mm, Waters Corporation, part number 186003117, serial number 0151323062
2) Clear target DPTM HPLC vials with pre-slit tef/white silicone septa caps; 100/pk, National Scientific, part number C4000-95P
3) Scintillation vials and caps; 20 mL low background borosilicate glass vial, polypropylene cap with metal foil liner; Research Products International Corp., part number 121000W0
4) Nylon membrane filter; Millipore, 0.2 µm GNWP, part number GNWP04700

Equipment

The equipment used throughout these examples is as follows:
1) INST-004 2695 Alliance separations module, Waters Corporation
2) INST-005 2487 Dual wavelength absorbance detector, Waters Corporation
3) INST-006 Column heater, Waters Corporation
4) INST-021 Retriever IV fraction collector, Isco
5) INST-025 Retriever IV fraction collector, Isco
6) INST-033 Retriever IV fraction collector, Isco
7) INST-023 Heated water bath, Thermo
8) INST-027 Heated water bath, Thermo
9) INST-031 Heated water bath, Thermo
10) INST-026 Heated circulating water bath, Fisher Scientific
11) INST-030 Heated circulating water bath, VWR International
12) INST-028 16 channel pump, Watson Marlow
13) INST-032 16 channel pump, Watson Marlow
14) INST-034 16 channel pump, Watson Marlow
15) INST-064 Model S slimline dermatome, Integra Life Sciences
16) INST-072 Balance, Sartorius
17) INST-078 Pump, KNF Laboport
18) INST-083 Caliper spring micrometer, Mitutoyo Corporation
19) INST-088 DIamond™ UV/UF NANOpure® system, Barnstead International
20) INST-116 AB15 pH meter, Fisher Scientific Opioid Preparation Oxymorphone base was obtained from commercial oxymorphone hydrochloride by reacting an aqueous solution of the oxymorphone hydrochloride with an aqueous solution of sodium hydroxide. The resulting precipitate was filtered off, washed twice with water and dried overnight under high vacuum.

Receiver Fluids

Isotonic phosphate buffer pH 6.3 was prepared by combining 1600 mL of a 0.067 M potassium phosphate, monobasic solution to 400 mL of a 0.13 M potassium phosphate, dibasic trihydrate solution. 4.4 g/L sodium chloride was then added to the buffer. The resulting mixture had a measured pH of 6.3. The water was obtained from a NANOpure® Diamond™ Life Science (UV/UF) ultrapure water system. The phosphate buffer was filtered (0.2 pm nylon membrane filter) and placed in a 2 L glass bottle.

A 10% ethanol in water receiver solution was prepared by adding 210 mL of ethyl acohol (190 Proof) to 1790 mL NANOpure® water. The receiver solution was then filtered (0.2 μm nylon membrane filter) and placed in a 2 L glass bottle.

Skin Preparation

Full thickness abdominal tissue with attached fat, harvested from abdominoplasty, was received. Skin was dermatomed (Model S slimline dermatome) to a thickness of ~250 μm. Dermatomed skin was stored at −20° C. until used for the permeation studies.

Permeation Studies

A PermeGear flow-through (In-Line, Hellertown, Pa.) diffusion cell system with supports was used for the skin permeation studies. The following protocol was used:

Diffusion cells were kept at 32° C. with a heated circulating water bath. The transdermal drug delivery system circular disc was placed on the skin and pressed down to ensure secure contact with the skin. Human skin was arranged in the diffusion cell with epidermis (upper layer of skin) facing the donor compartment. Each cell was charged with a circular disc cut (0.95 cm$^2$) from the respective transdermal drug delivery system. Permeation area of the skin was 0.95 cm$^2$. Diffusion cells remained uncovered to mimic clinical conditions for the duration of the study. Data was collected from a single human skin donor with 3-4 diffusion cells per formulation.

Receiver solution was initially a pH 6.3 isotonic phosphate buffer but was later switched to 10% aqueous ethanol. The flow rate was set to ~1.1 mL/h in order to help maintain sink conditions.

Samples were collected into scintillation vials at 8, 16, 24, 32, 40, 48, 56, 64 and 72 hour time points.

At the end of the 72 hour experiment, the skin concentrations were determined and patches were extracted.

The diffusion samples were analysed the day of collection or the following day.

Dose Administration

A 0.95 cm$^2$ circular disc from the respective transdermal drug delivery system was cut to fit the In-line diffusional area. The 0.95 cm$^2$ transdermal drug delivery system circular disc was placed on the skin and pressed down to ensure secure contact with the skin. Once cells were equilibrated, the study was initiated by starting the fraction collector and collecting fractions for the respective time increments.

Analytical Methods

Quantification of oxymorphone was done by high performance liquid chromatography (HPLC). Briefly, HPLC was conducted on a Waters 2695 Alliance separations module and column heater with a 2487 dual wavelength absorbance detector. The solvent system consisting of 35% A) acetonitrile and 65% B) phosphate buffer, pH 8.0 was run through a Waters XBridge® C$_{18}$ 5 μm, 4.6×250 mm column at a flow rate of 1.0 mL/min. 50 μL of the diffusion samples and 20 μL for the skin samples were injected onto the HPLC column. The limit of detection was 0.043 μg/mL. Samples were analysed the day of collection or the following day.

Example 1

Opioid Layer

Typical Preparation of Oxymorphone Formulations

The following series of steps provide a typical protocol for the preparation of the oxymorphone formulations forming part of the invention (in this specific example, the preparation of a 5% oxymorphone matrix layer (1 kg)). Materials and amounts may vary depending on specific composition of formulations.

1. Weigh 50 g oxymorphone base into a mixing vessel (5% w/w).
2. Tare weight and add 100 g of oleic acid, NF to the vessel (10% w/w).
3. Pipet 60 mL of ethanol (200 proof) into the vessel.
4. Pipet 260 mL of ethyl acetate into the vessel.
5. Begin mixing and blend until and oxymorphone is completely dissolved.
6. Add 242.1 g Duro-Tak® 9301 (non-volatile content (NVC=41.3%) (10% w/w).
7. Add 1219.5 kg Dow® BIO-PSA 7-4302 (non-volatile content (NVC=61.5%) (75% w/w).
8. Blend until a homogenous viscous solution is achieved.
9. Extrude at 20 mil wet thickness onto 3M™ Scotchpak™ 1022 release liner and air dry for 15 minutes at 25° C.
10. Oven dry at 90° C. for 15 minutes.
11. Laminate with 3M™ Scotchpak™ 1022 release liner and reroll for the complete patch assembly.
12. Store desiccated until ready for use.

Oxymorphone Formulations

The composition of exemplary oxymorphone formulations are summarized below. Formulations were prepared on a 1 gram scale. Addition of solvent, ethanol and ethyl acetate were added to enhance solubility and mixing of solid excipients.

OM-2014-01-001

3% Oxymorphone
97% Dow Corning® BIO-PSA 7-4502
100 μL Ethanol

OM-2014-01-002

3% Oxymorphone
97% Dow Corning® BIO-PSA 7-4302 (amine compatible)
100 μL Ethanol

OM-2014-01-003

8% Oxymorphone
92% Duro-Tak® 2054 Acrylic (—COOH functional group)
100 μL Ethanol

OM-2014-01-004

3% Oxymorphone
97% Duro-Tak® 4098 Acrylic (non-functional group)
100 μL Ethanol

OM-2014-01-005

3% Oxymorphone
97% Duro-Tak® 608A Polyisobutylene [PIB]
100 μL Ethanol

OM-2014-01-006

6% Oxymorphone
94% Duro-Tak® 202A Acrylic (—OH functional group)
100 μL Ethanol

-continued

OM-2014-01-007

5% Oxymorphone
95% Dow Corning ® BIO-PSA 7-4302/Duro-Tak ® 2054
Acrylic (80:20)
150 µL Ethanol
OM-2014-01-008

5% Oxymorphone
89% Dow Corning ® BIO-PSA 7-4302/Duro-Tak ® 2054
Acrylic (80:20)
6% Lactic acid
150 µL Ethanol
OM-2014-01-009

5% Oxymorphone
5% Polyvinylpyrollidone [PVP-K30] (MW 30,000)
5% Polyvinylpyrollidone vinyl acetate [PVP-VA]
7.5% Myristic acid
70.5% Dow Corning ® BIO-PSA 7-4302:BIO-PSA 7-4202 (75:25)
7% Duro-Tak ® 9301
60 µL Ethanol
260 µL Ethyl acetate
OM-2014-01-010

5% Oxymorphone
5% Polyvinylpyrollidone [PVP-K30] (MW 30,000)
5% Polyvinylpyrollidone vinyl acetate [PVP-VA]
5% Myristic acid
7.5% Myristyl myristate
65.5% Dow Corning ® BIO-PSA 7-4302:BIO-PSA 7-4202 (75:25)
7% Duro-Tak ® 9301
60 µL Ethanol
260 µL Ethyl acetate
OM-2014-01-011

5% Oxymorphone
2.5% Polyvinylpyrollidone [PVP-K30] (MW 30,000)
2.5% Polyvinylpyrollidone vinyl acetate [PVP-VA]
7.5% Oleic acid
10% Propylene glycol
65.5% Dow Corning ® BIO-PSA 7-4302:BIO-PSA 7-4202 (75:25)
7% Duro-Tak ® 9301
60 µL Ethanol
260 µL Ethyl acetate
OM-2014-01-012

5% Oxymorphone
2.5% Polyvinylpyrollidone [PVP-K30] (MW 30,000)
2.5% Polyvinylpyrollidone vinyl acetate [PVP-VA]
7.5% Oleic acid
5% Propylene glycol
70.5% Dow Corning ® BIO-PSA 7-4302:BIO-PSA 7-4202 (75:25)
7% Duro-Tak ® 9301
60 µL Ethanol
260 µL Ethyl acetate
OM-2014-01-013

5% Oxymorphone
2.5% Polyvinylpyrollidone [PVP-K30] (MW 30,000)
2.5% Polyvinylpyrollidone vinyl acetate [PVP-VA]
7.5% Myristic acid
5% Propylene glycol
70.5% Dow Corning ® BIO-PSA 7-4302:BIO-PSA 7-4202 (75:25)
7% Duro-Tak ® 9301
60 µL Ethanol
260 µL Ethyl acetate
OM-2014-01-014

5% Oxymorphone
7.5% Oleic acid
87.5% Dow Corning ® BIO-PSA 7-4302
60 µL Ethanol
260 µL Ethyl acetate -continued

OM-2014-01-015

5% Oxymorphone
5% Polyvinylpyrollidone [PVP-K30] (MW 30,000)
7.5% Oleic acid
82.5% Dow Corning ® BIO-PSA 7-4302
60 µL Ethanol
260 µL Ethyl acetate
OM-2014-01-016

5% Oxymorphone
5% Polyvinylpyrollidone [PVP-K30] (MW 30,000)
7.5% Oleic acid
7.5% Propylene glycol
75% Dow Corning ® BIO-PSA 7-4302
60 µL Ethanol
200 µL Ethyl acetate
OM-2014-01-017

5% Oxymorphone
5% Polyvinylpyrollidone vinyl acetate [PVP-VA]
7.5% Oleic acid
7.5% Propylene glycol
75% Dow Corning ® BIO-PSA 7-4302
60 µL Ethanol
200 µL Ethyl acetate
OM-2014-01-018

5% Oxymorphone
2.5% Polyvinylpyrollidone [PVP-K30] (MW 30,000)
2.5% Polyvinylpyrollidone vinyl acetate [PVP-VA]
5% Oleic acid
7.5% Propylene glycol
77.5% Dow Corning ® BIO-PSA 7-4302
60 µL Ethanol
200 µL Ethyl acetate
OM-2014-01-019

5% Oxymorphone
2.5% Polyvinylpyrollidone [PVP-K30] (MW 30,000)
2.5% Polyvinylpyrollidone vinyl acetate [PVP-VA]
5% Oleic acid
7.5% Propylene glycol
67.5% Dow Corning ® BIO-PSA 7-4302:BIO-PSA 7-4202 (75:25)
10% Duro-Tak ® 9301
60 µL Ethanol
200 µL Ethyl acetate
OM-2014-01-020

5% Oxymorphone
7.5% Oleic acid
87.5% Dow Corning ® BIO-PSA 7-4302
50 µL Ethanol
150 µL Ethyl acetate
OM-2014-01-021

5% Oxymorphone
7.5% Oleic acid
2.5% Propylene glycol
75% Dow Corning ® BIO-PSA 7-4302
10% Duro-Tak ® 9301
50 µL Ethanol
150 µL Ethyl acetate
OM-2014-01-022

5% Oxymorphone
7.5% Oleic acid
77.5% Dow Corning ® BIO-PSA 7-4302
10% Duro-Tak ® 9301
60 µL Ethanol
200 µL Ethyl acetate
OM-2014-01-023

5% Oxymorphone
7.5% Oleic acid
2.5% Propylene glycol
77.5% Dow Corning ® BIO-PSA 7-4302
10% Duro-Tak ® 9301

-continued

60 μL Ethanol
200 μL Ethyl acetate
OM-2014-01-024

3.5% oxymorphone
7.5% oleic acid
77.5% Dow Corning BIO-PSA 7-4302
11.5% Duro-tak 9301
60 ul Ethanol
200 ul ethyl acetate
OM-2014-01-025

5% oxymorphone
8.5% myristic acid
76.5% Dow Corning BIO-PSA 7-4302
10% Duro-tak 9301
60 ul Ethanol
200 ul ethyl acetate
OM-2014-01-028

5% Oxymorphone
10% oleic acid
75% Dow Corning BIO-PSA 7-4302
10% Duro-tak 9301
60 ul Ethanol
260 ul ethyl acetate
OM-2014-01-030

5% Oxymorphone
10% oleic acid
75% Dow Corning BIO-PSA 7-4302
10% Duro-tak 9301
155 ul Ethanol
155 ul ethyl acetate
OM-2014-01-043

5% oxymorphone
7.5% oleyl alcohol
5% PVP K30
82.5% Duro-Tak 4098
400 ul ethanol
100 ul EtOAc
OM-2014-01-046

5% Oxymorphone
10% (1:1 oleic acid:oleyl alcohol)
5% PVP-K30
80% Duro-tak 4098
OM-2014-01-047

5% Oxymorphone
10% (1:1 ethyl oleate:oleyl alcohol)
5% PVP-K30
80% Duro-tak 4098
OM-2014-01-048

5% Oxymorphone
10% (1:1 oleyl oleate:oleyl alcohol)
5% PVP-K30
80% Duro-tak 4098

Oxymorphone Formulation Test Data

FIG. 1 and Table 1 below provide permeation data of oxymorphone formulation OM-2014-01-011 (n=3) with pH 6.3 isotonic phosphate buffer receiver solution.

TABLE 1

Permeation data of oxymorphone formulation OM-2014-01-011 (n = 3) with pH 6.3 isotonic phosphate buffer receiver solution*

| Compound | 72 h skin concentration (μmol/g) | 72 h cumulative amount (μg) | Flux (μg/cm$^2$/h) |
|---|---|---|---|
| OM-2014-01-011 | 2.2 ± 0.2 | 544.3 ± 113.8 | 7.6 ± 2.0 |

*One cell was removed from data set (outlier)

Figure 2:
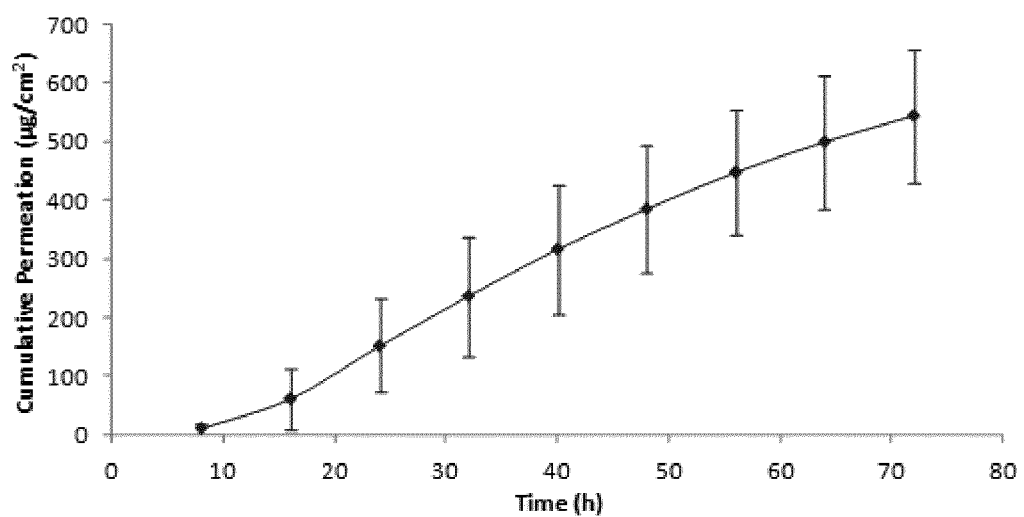
FIG. 2 shows the representative cumulative human skin permeation profile of oxymorphone formulation, OM-2014-01-011 (n=3)
Figure 3:
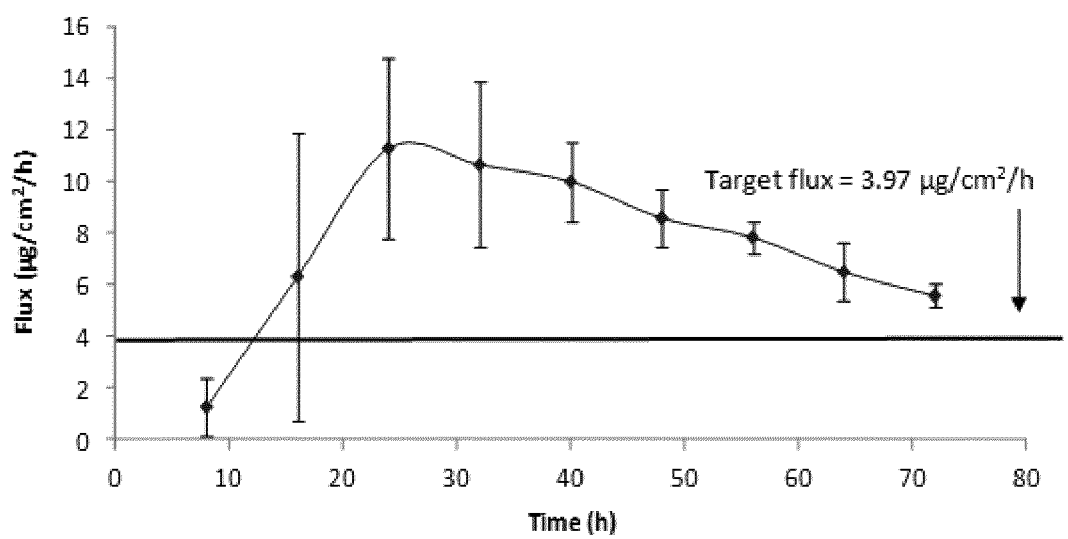
FIG. 3 shows the representative time interval flux values of oxymorphone formulation, OM-2014-01-011 (n=3)

FIG. 2 shows representative cumulative human skin permeation profile of oxymorphone formulation, OM-2014-01-011 (n=3). FIG. 3 shows representative time interval flux values of oxymorphone formulation, OM-2014-01-011 (n=3).

Figure 4:
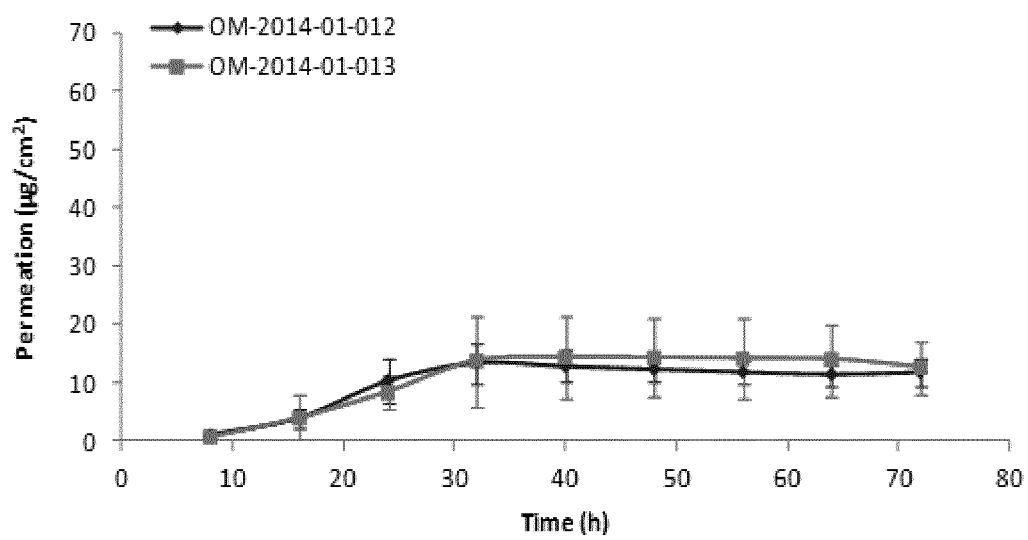
FIG. 4 shows the representative human skin permeation profile of oxymorphone formulations, OM-2014-01-012 (n=4) & OM-2014-01-013 (n=4)
Figure 5:
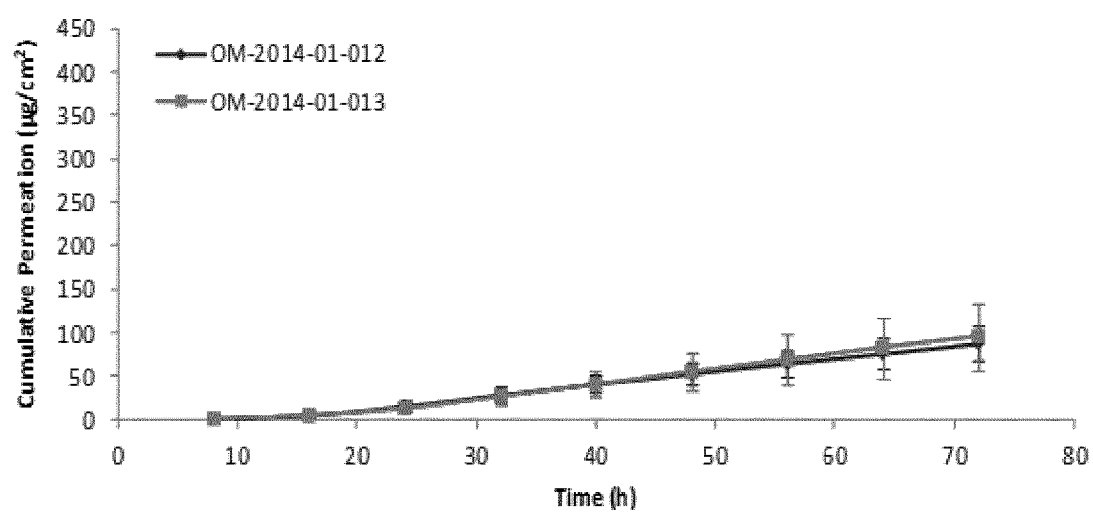
FIG. 5 shows the representative cumulative human skin permeation profile of oxymorphone formulations, OM-2014-01-012 (n=4) & OM-2014-01-13 (n=4)
Figure 6:
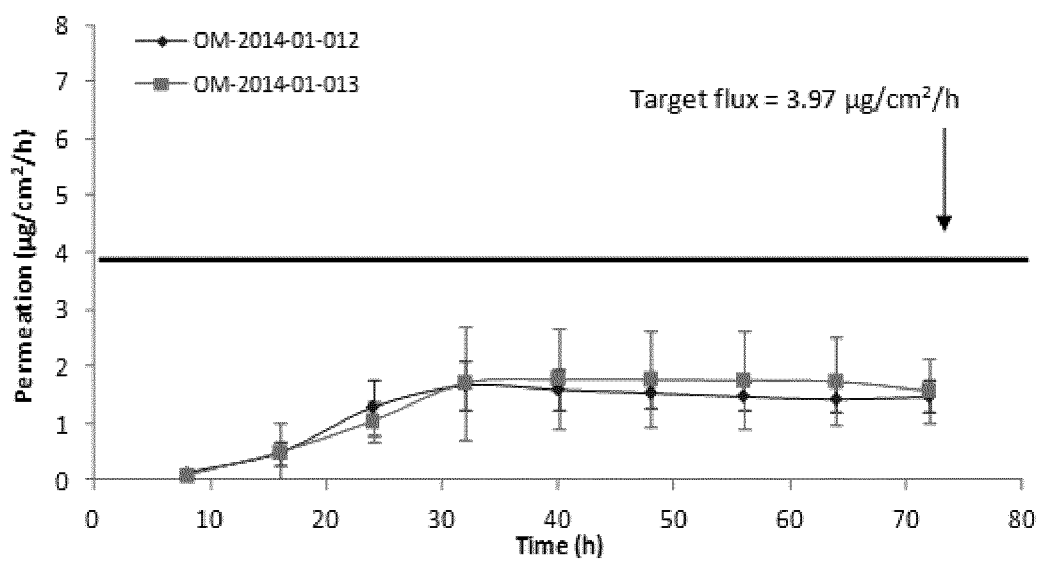
FIG. 6 shows the representative time interval flux values of oxymorphone formulation, OM-2014-01-012 (n=4) and OM-2014-01-013 (n=4)

Formulations OM-2014-01-012 and OM-2014-01-013 focused on decreasing propylene glycol (PG) content by 5% in both formulations while holding constant the PVP-K30, PVP-VA, and acid concentration. Reduction of PG to 5% decreased permeation as compared to formulation OM-2014-01-011. This reduction in PG content may have influenced the permeability of oxymorphone out of the matrix by creating a more non porous pathway due to an overall increase in solid content. Results are shown in Table 2 and FIGS. 4, 5, and 6 for OM-2014-01-012 and OM-2014-01-013.

TABLE 2

Permeation data of oxymorphone formulation OM-2014-01-012 (n = 4) & OM-2014-01-013 (n = 4) with 10% aqueous ethanol receiver solution

| Compound | 72 h skin concentration (μmol/g) | 72 h cumulative amount (μg) | Flux (μg/cm$^2$/h) |
|---|---|---|---|
| OM-2014-01-012 | ND | 88.0 ± 18.9 | 1.2 ± 0.3 |
| OM-2014-01-013 | ND | 95.2 ± 39.4 | 1.3 ± 0.7 |

ND = none determined

Figure 7:
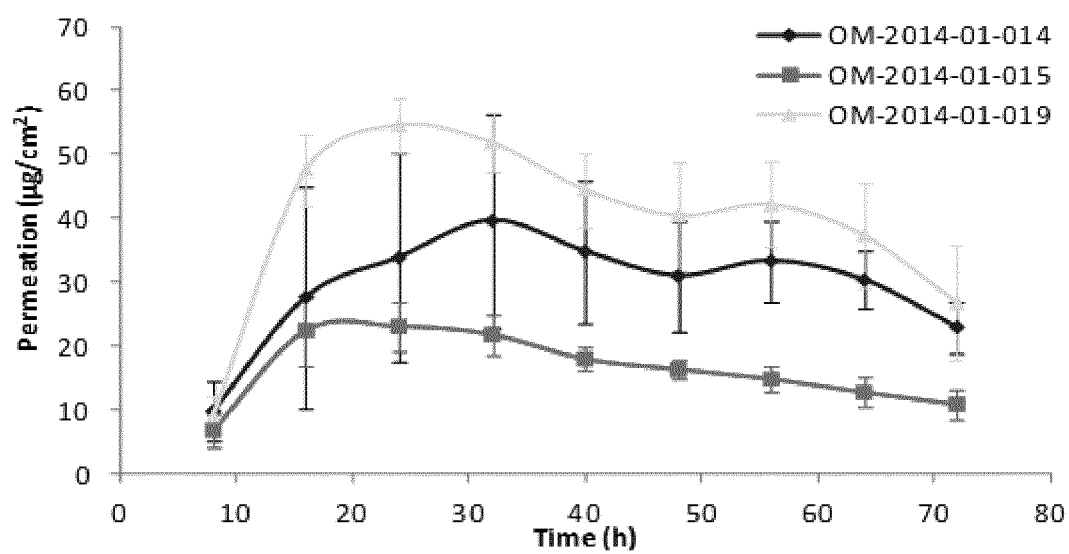
FIG. 7 shows the representative human skin permeation profile of oxymorphone formulations, OM-2014-01-014 (n=4), OM-2014-01-015 (n=4) & OM-2014-01-019 (n=4)
Figure 8:
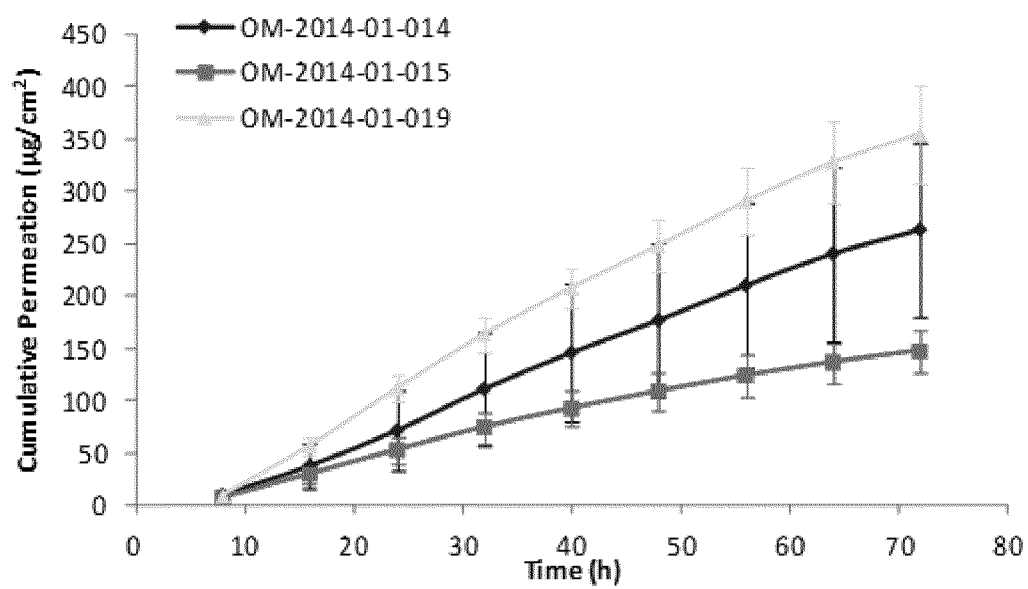
FIG. 8 shows the representative cumulative human skin permeation profile of oxymorphone formulations, OM-2014-01-014 (n=4), OM-2014-01-015 (n=4) & OM-2014-01-019 (n=4)
Figure 9:
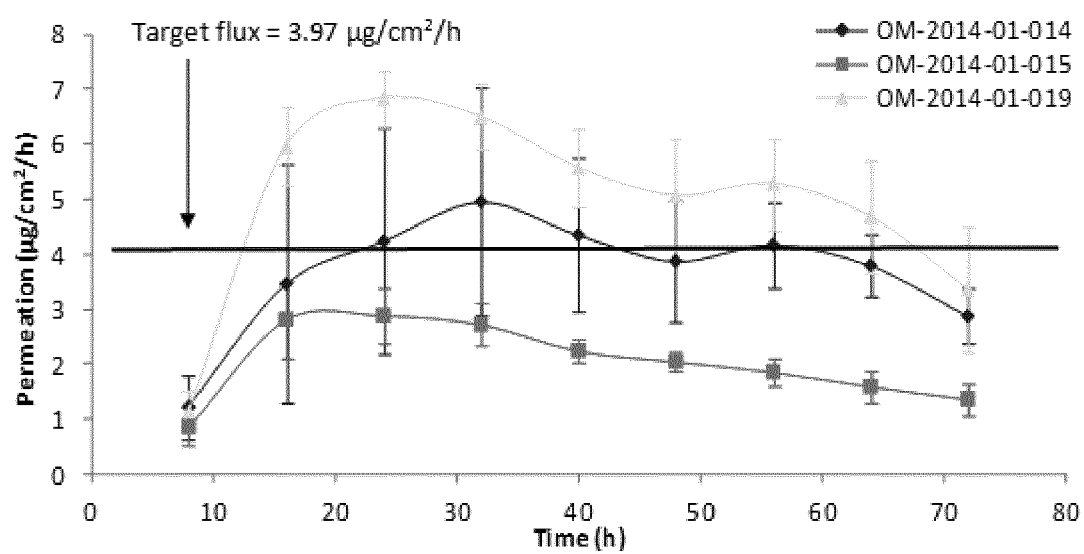
FIG. 9 shows the representative time interval flux values of oxymorphone formulation, OM-2014-01-014 (n=4), OM-2014-01-015 (n=4), and OM-2014-01-019 (n=4)

Despite being viable opioid formulations, formulations OM-2014-01-016, OM-2014-01-017, and OM-2014-01-018 were not tested for inclusion in a transdermal patch due to non-uniform matrix formulation when cast onto the release liner and dried. Formulations OM-2014-01-014 and OM-2014-01-015 were more white in appearance than other formulations when mixed and uniform casts prepared; however upon observation after drying, no solid particulates were observed. The addition of Duro-Tak® 9301 to formulation OM-2014-01-019 provided enhanced solubility upon mixing; therefore a more transparent film was observed upon casting and drying. Results are shown in Table 3 and FIGS. 7, 8, and 9 for OM-2014-01-014, OM-2014-01-015, and OM-2014-01-019.

TABLE 3

Permeation data of oxymorphone formulation OM-2014-01-014 (n = 4), OM-2014-01-015 (n = 4), & OM-2014-01-019 (n = 4) with 10% aqueous ethanol receiver solution

| Compound | 72 h skin concentration (μmol/g) | 72 h cumulative amount (μg) | Flux (μg/cm$^2$/h) |
|---|---|---|---|
| OM-2014-01-014 | 22.7 ± 8.8 | 263.5 ± 82.8 | 3.7 ± 1.3 |
| OM-2014-01-015 | 7.5 ± 1.1 | 147.4 ± 19.8 | 2.1 ± 0.4 |
| OM-2014-01-019 | 14.2 ± 5.0 | 355.2 ± 47.2 | 4.9 ± 0.8 |

Figure 10:
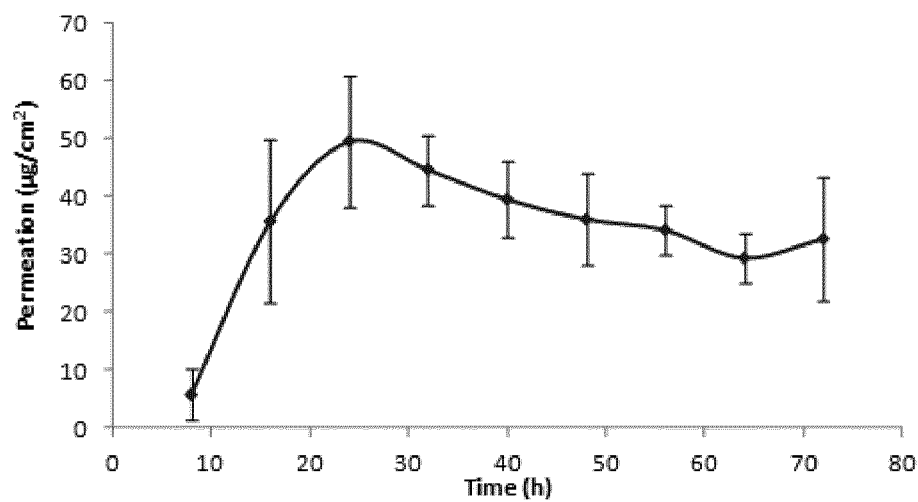
FIG. 10 shows the representative human skin permeation profile of oxymorphone formulation, OM-2014-01-014 (n=4), different skin donor (repeat study)
Figure 11:
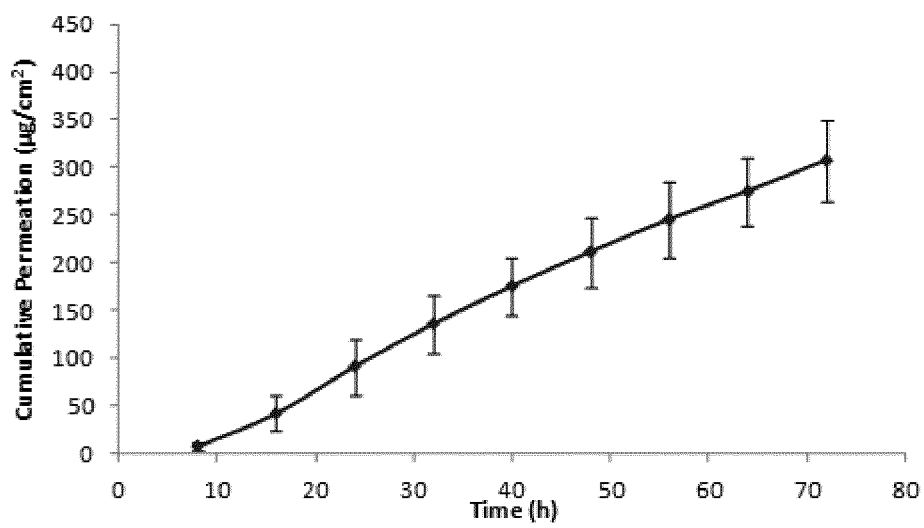
FIG. 11 shows the representative cumulative human skin permeation profile of oxymorphone formulation, OM-2014-01-014 (n=4), different skin donor (repeat study)
Figure 12:
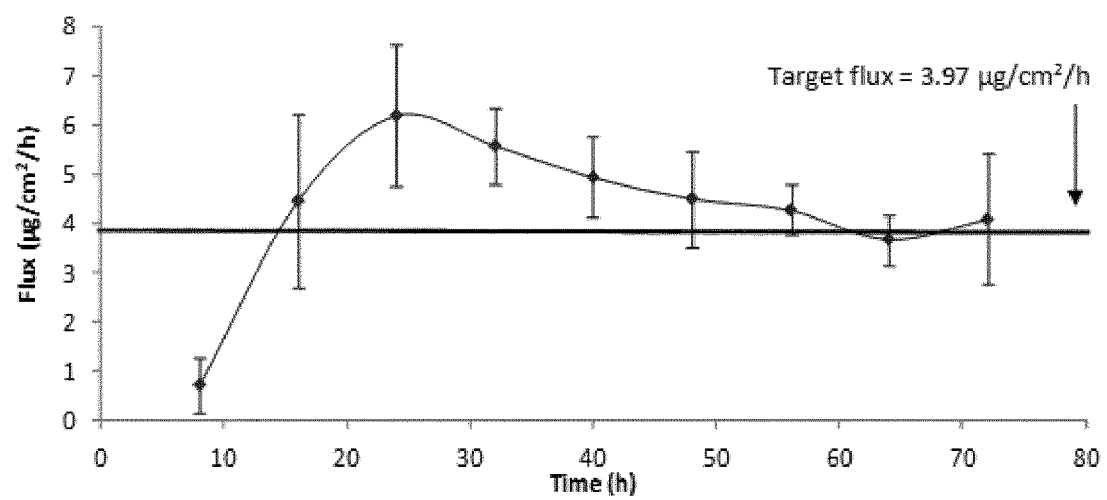
FIG. 12 shows the representative time interval flux values of oxymorphone formulation, OM-2014-01-014 (n=4), different skin donor (repeat study)

Based on initial positive results, formulation OM-2014-01-014 was repeated on a different skin donor to confirm the flux value. Even though OM-2014-01-019 had a higher flux value compared to OM-2014-01-014, OM-2014-01-019 was not repeated due to the relative complexity of the formulation. Results are shown in Table 4 and FIGS. 10, 11, and 12 for OM-2014-01-014.

TABLE 4

Permeation data of oxymorphone formulation OM-2014-01-014
(n = 4), on a different skin donor for flux confirmation
with 10% aqueous ethanol receiver solution (repeat study)

| Compound | 72 h skin concentration (μmol/g) | 72 h cumulative amount (μg) | Flux (μg/cm²/h) |
|---|---|---|---|
| OM-2014-01-014 | 18.2 ± 4.8 | 307.0 ± 42.5 | 4.3 ± 1.0 |

Figure 13:
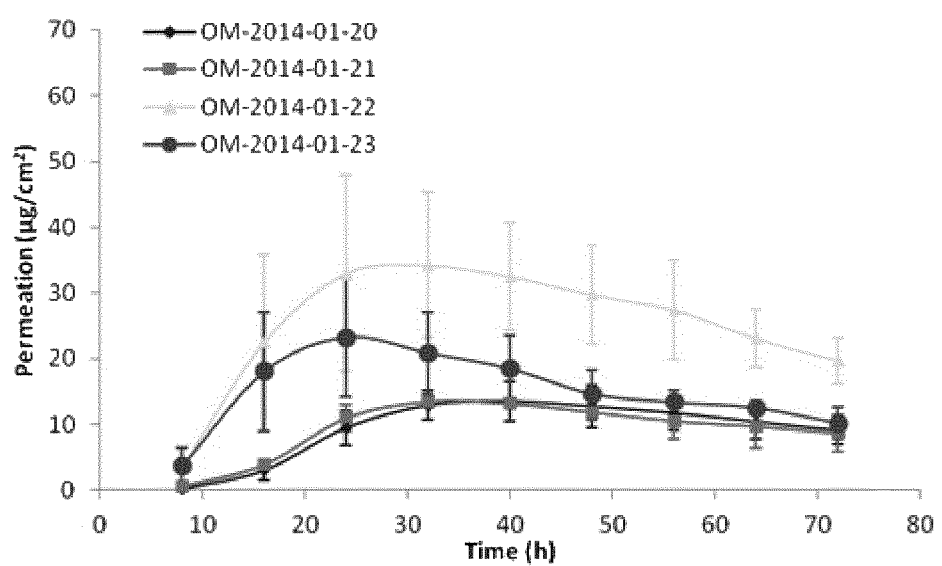
FIG. 13 shows the representative human skin permeation profile of oxymorphone formulations, OM-2014-01-020 (n=3), OM-2014-01-021 (n=3), OM-2014-01-022 (n=3) & OM-2014-01-023 (n=3)
Figure 14:
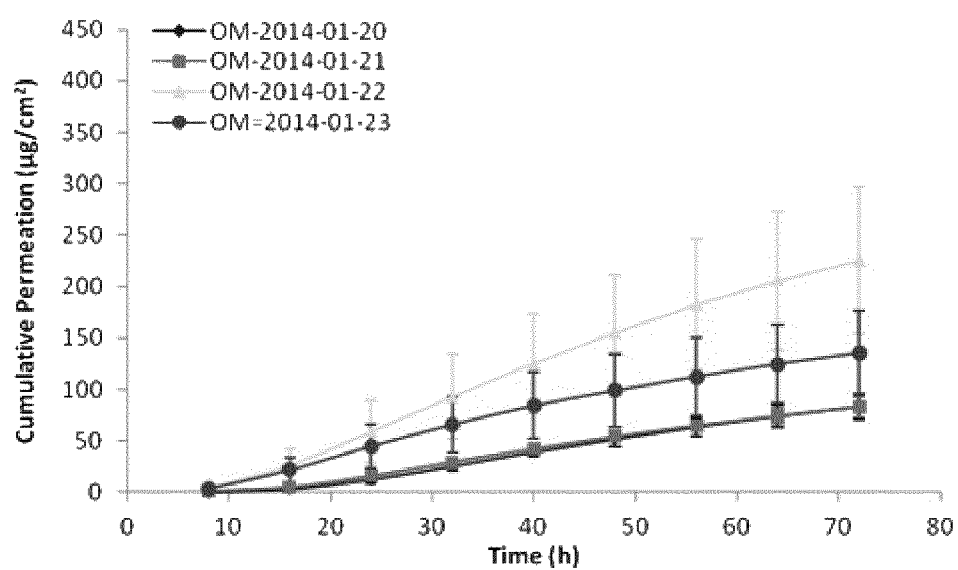
FIG. 14 shows the representative cumulative human skin permeation profile of oxymorphone formulations, OM-2014-01-020 (n=3), OM-2014-01-021 (n=3), OM-2014-01-022 (n=3) & OM-2014-01-023 (n=3)
Figure 15:
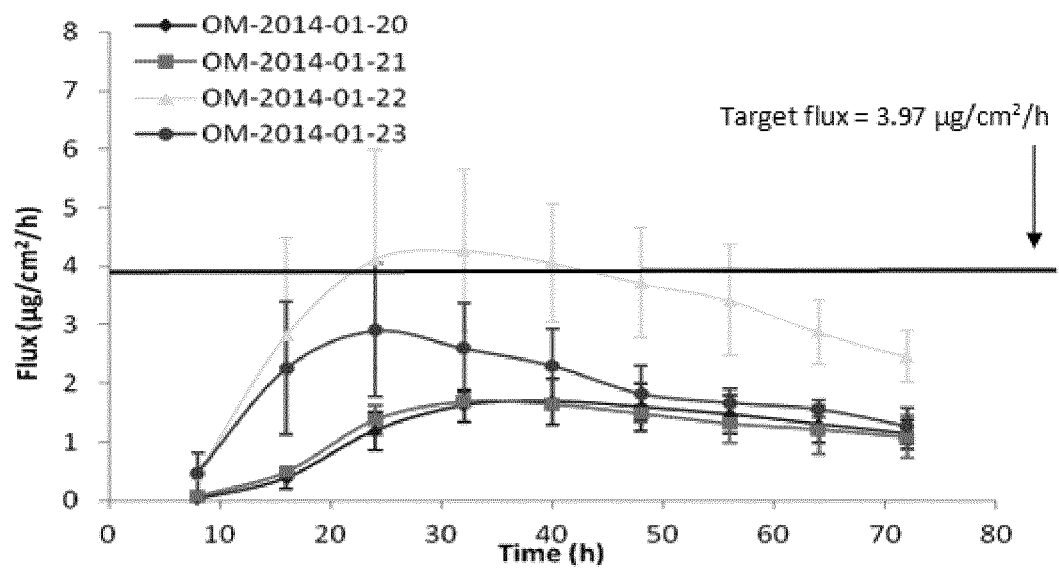
FIG. 15 shows the representative point flux estimations of oxymorphone formulations, OM-2014-01-020 (n=3), OM-2014-01-021 (n=3), OM-2014-01-022 (n=3) & OM-2014-01-023 (n=3)

Formulations OM-2014-01-020, OM-2014-01-021, OM-2014-01-022, and OM-2014-01-023 were prepared in order to investigate small differences in amounts of additional ethanol and ethyl acetate as well as the addition of PG and Duro-Tak® 9301 into the formulation. Initially, formulations OM-2014-01-020 and OM-2014-01-021 were to be prepared with no addition of ethanol or ethyl acetate; however, mixing was difficult and a minimal amount was added. Both formulations were cast at 15 mil wet thickness compared to 20 mil wet thickness of all previous formulations and formulations, OM-2014-01-022 and OM-2014-01-023. Formulation OM-2014-01-022 showed the best results, with an average flux of 3.1±1.0 pg/cm²/h. This formulation containing 10% Duro-Tak® 9301 will provide better wear during therapy and was therefore selected for further studied along with OM-2014-01-014 for flux and with the abuse deterrent platform. Results are shown in Table 5 and FIGS. 13, 14, and 15 for OM-2014-01-020, OM-2014-01-021, OM-2014-01-022, and OM-2014-01-23.

TABLE 5

Permeation data of oxymorphone formulation OM-2014-
01-020 (n = 3), OM-2014-01-021 (n = 3),
OM-2014-01-022 (n = 3) & OM-2014-01-023 (n =
3) with 10% aqueous ethanol receiver solution

| Compound | 72 h skin concentration (μmol/g) | 72 h cumulative amount (μg/cm²) | Flux (μg/cm²/h) |
|---|---|---|---|
| OM-2014-01-020 | 12.4 ± 1.9 | 83.0 ± 12.6 | 1.2 ± 0.3 |
| OM-2014-01-021 | 9.7 ± 4.9 | 83.0 ± 9.7 | 1.2 ± 0.2 |
| OM-2014-01-022 | 10.1 ± 13.2 | 225.6 ± 71.5 | 3.1 ± 1.0 |
| OM-2014-01-023 | 2.6 ± 1.3 | 135.0 ± 40.9 | 1.9 ± 0.6 |

A variety of adhesive systems, enhancers and cosolvents were employed to observe permeation differences within these systems. In general, solubility in acrylic adhesives (i.e. Duro-Tak®) was higher, and thus the driving force out of the patch would be relatively lower. Solubility in silicone adhesives was lower and thus provided a much higher driving constant out of the formulation and into the skin; however, due to the relatively lower solubility, a solubility enhancer that also assisted in solubilising the skin was utilized. Three acids (lactic acid (MW: 90.08), myristic acid (MW: 228.38) and oleic acid (MW: 282.47)) were screened for permeation and solubility enhancement. Oleic acid, the most hydrophobic acid screened, almost immediately dissolved 5% w/w OXY during formulation preparation and provided enhancement to obtain the desired permeation rate. Oleic acid is currently approved in 6 topical and transdermal formulations according to the FDA's inactive ingredient list. Owing to their fewer number of additives that may have a negative effect of cohesive properties, an opiate containing layer such as OM-2014-01-014 or OM-2014-01-022 provides preferred wear characteristics as well as delivery rates.

For oxymorphone, the required therapeutic flux value is 3.97 μg/cm²/h for a 42 cm² transdermal drug delivery system (see Table 6 below). Currently with formulation OM-2014-01-014, the flux value is 4.0±1.2 μg/cm²/h (n=8). The cumulative permeation of oxymorphone is 285.3±65.2 μg/cm² (n=8). Based on these results, a 42 cm² transdermal drug delivery system would delivery at the therapeutic levels for 3 days. The estimated drug load per patch would be 38.2 mg for a 42 cm² patch.

The apparent lag time for all formulations ranged from 16-24 h based on point flux estimation calculations. That is, lag time was estimated from the point at which flux over time became statistically constant.

Time increments of 8 h for 72 h duration were chosen for initial screening. Time increments as described in the proposal will be used for completing the in vitro permeation studies with the optimized formulation(s).

TABLE 6

Comparison of parameters for opioids

| Parameters | Oxycodone | Oxymorphone | Hydrocodone | Hydromorphone |
|---|---|---|---|---|
| Oral dose (mg/day) | 80.0 | 40.0 | 80.0 | 45.5 |
| Bioavailability | 87% | 10% | 80% | 24% |
| Dose after first pass effect (mg/day) | 69.6 | 4.0 | 64.0 | 10.9 |
| Patch size | 140 | 42 | 140 | 40 |
| Required flux* (μg/cm²/h) | 20.7 | 3.97 | 19.0 | 11.4 |

*Required flux was derived from the following equation based on daily dose, bioavailability and a theoretical patch size $$\text{Required Flux} \left(\frac{\mu g}{cm^2 \cdot h}\right) = \frac{\text{Dose}\left(\frac{mg}{day}\right) \times \text{Bioavailability}(\%)}{\text{Theoretical patch size } (cm^2) \times \text{Time}\left(\frac{24 \text{ h}}{1 \text{ day}}\right)} \times 1000 \frac{\mu g}{mg}$$

$$\text{Oxymorphone Required Flux} \left(\frac{\mu g}{cm^2 \cdot h}\right) = \frac{40 \left(\frac{mg}{day}\right) \times 10 \, (\%)}{42 \, (cm^2) \times \left(\frac{24 \text{ h}}{1 \text{ day}}\right)} \times 1000 \frac{\mu g}{mg}$$

$$\text{Oxymorphone Required Flux} \left(\frac{\mu g}{cm^2 \cdot h}\right) = 3.97 \frac{\mu g}{cm^2 \cdot h}$$

Dual Penetration Enhancer Formulations

Formulations comprising dual penetration enhancers were investigated. Exemplified enhancers included combinations of oleyl alcohol and either (i) oleic acid; (ii) ethyl oleate and (iii) oley oleate. Formulations comprising dual enhancers include OM-01-043; OM-01-046; OM-01-047 and OM-01-048.

Figure 16:
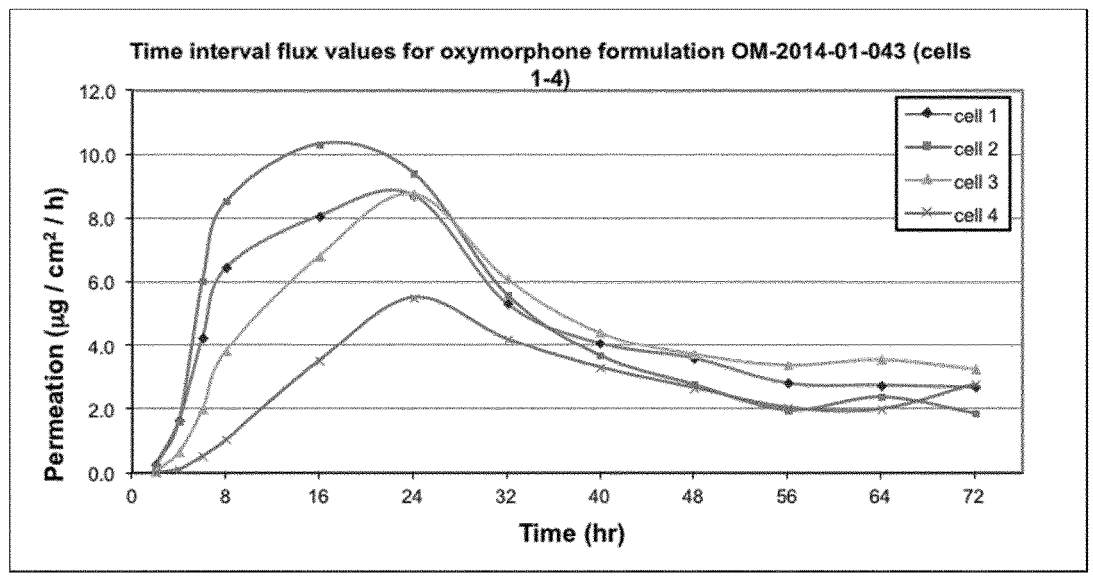
FIG. 16 shows the representative human skin permeation profile of oxymorphone formulation, OM-2014-01-043 (n=4).
Figure 17:
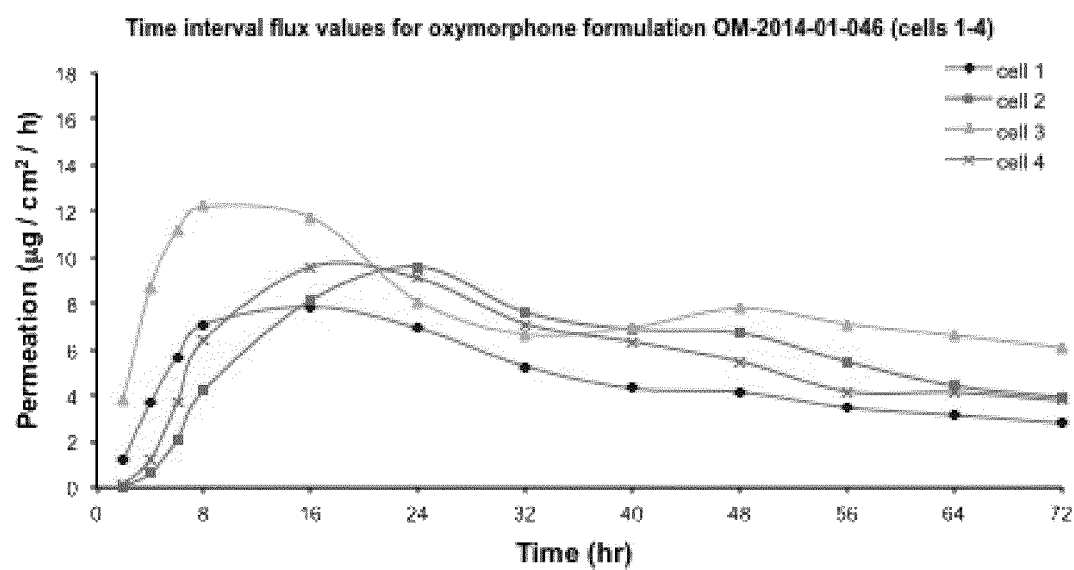
FIG. 17 shows the representative human skin permeation profile of oxymorphone formulation, OM-2014-01-046 (n=4) (pig skin).

All of the above formulations were cast and flux values were determined in pig skin and in human skin. The results are summarised in Table 7 and FIGS. 16 and 17. All the exemplified dual penetration enhancer formulations demonstrated marked increases in flux when compared to other exemplified formulations.

TABLE 7

Summary of flux values for formulations OM-01-043; OM-01-046; OM-01-047 and OM-01-048

| Compound | Flux (μg/cm$^2$/h) (PIG) | Flux (μg/cm$^2$/h) (human) | | |
|---|---|---|---|---|
| OM-2014-01-043 | 4.2 ± 1.11 | n/a | | |
| OM-2014-01-046 | 6.09 ± 1.60 | 4.67 (65/w/f) | 4.32 (46/b/f) | 4.37 (59/w/f) |
| OM-2014-01-047 | 6.05 ± 1.12 | n/a | | |
| OM-2014-01-048 | 5.77 ± 1.10 | n/a | | |

Formulation (OM-01-046) was then subsequently tested in three different types of human skin. Three human donor skins were used. All skin donors were female.

Figure 18:
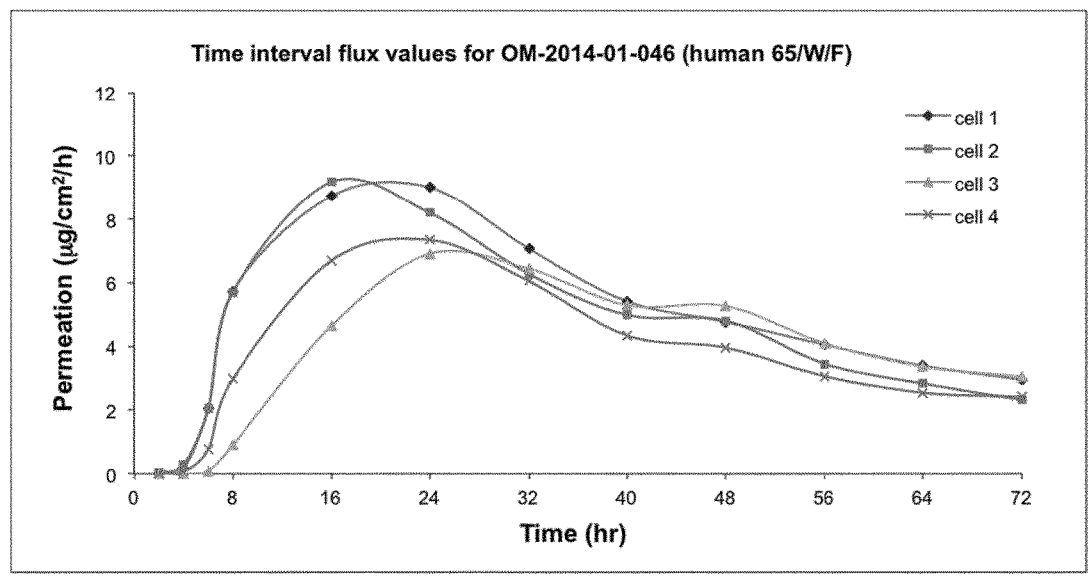
FIG. 18 shows the representative human skin permeation profile of oxymorphone formulation, OM-2014-01-046 (n=4) for skin donor one (white female, aged 65).

Skin donor one was white; aged 65 years. The flux was determined to be 4.67 ug/cm$^2$/hr. The results are shown in FIG. 18.

Figure 19:
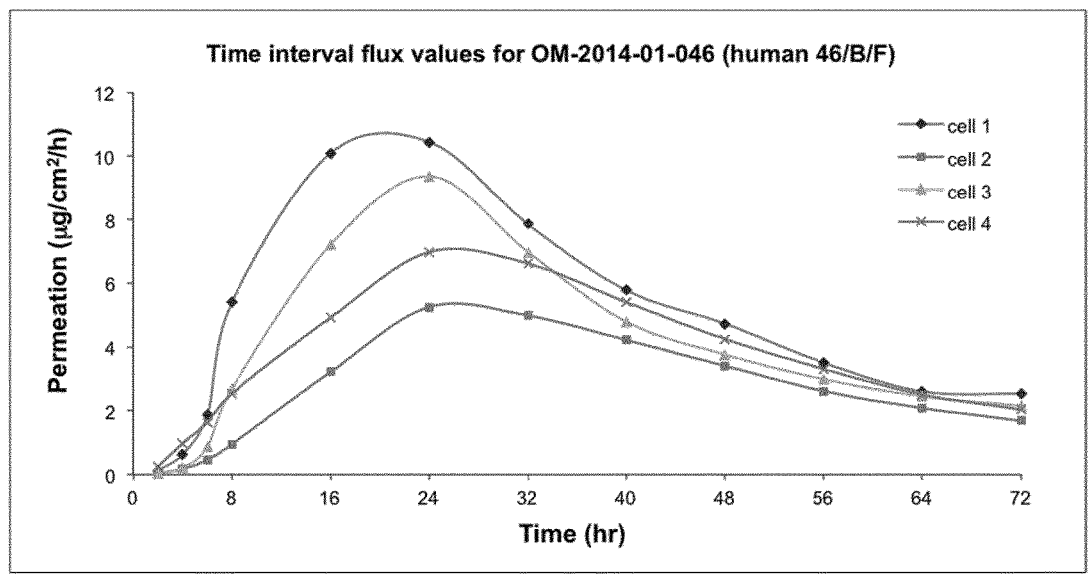
FIG. 19 shows the representative human skin permeation profile of oxymorphone formulations, OM-2014-01-046 (n=4) for skin donor two (black female, aged 46).

Skin donor two was black aged 46 years. The flux was determined to be 4.32 ug/cm$^2$/hr. The results are shown in FIG. 19.

Skin donor three was white aged 59 years. The flux was determined to be 4.37ug/cm$^2$/hr. The results are shown in FIG. 20.

Figure 20:
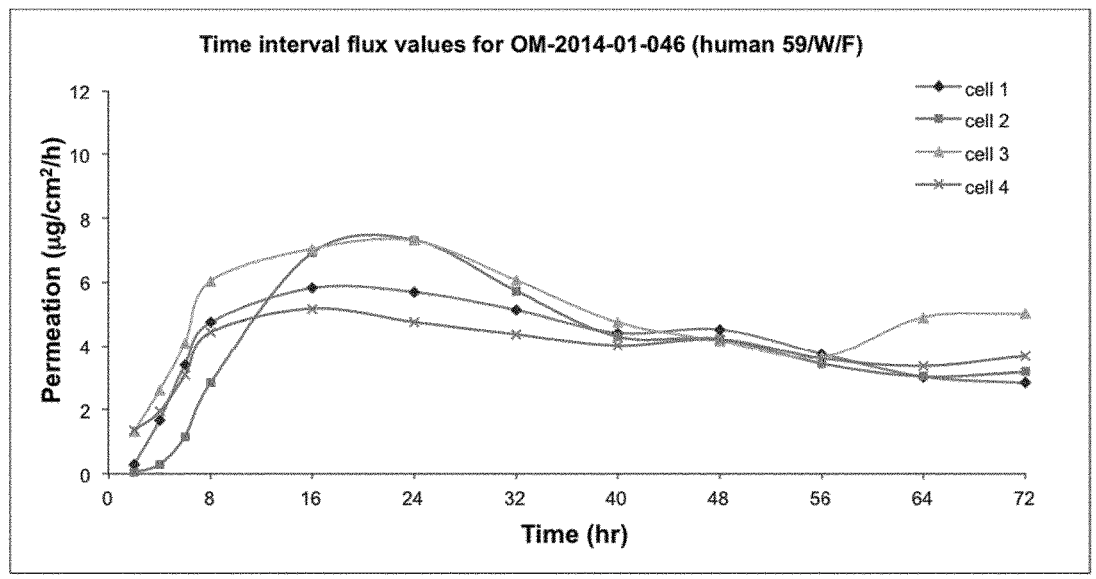
FIG. 20 shows the representative human skin permeation profile of oxymorphone formulations, OM-2014-01-046 (n=4) for skin donor three (white female, aged 59).

It should be noted that for FIG. 20 there was a leakage in cell 3 at the end of the experiment. Flux values for 64 h and 72 h are artificially elevated. Instead of these data points, the average of 48 and 56 h values were used for the average flux calculations.

Figure 21:
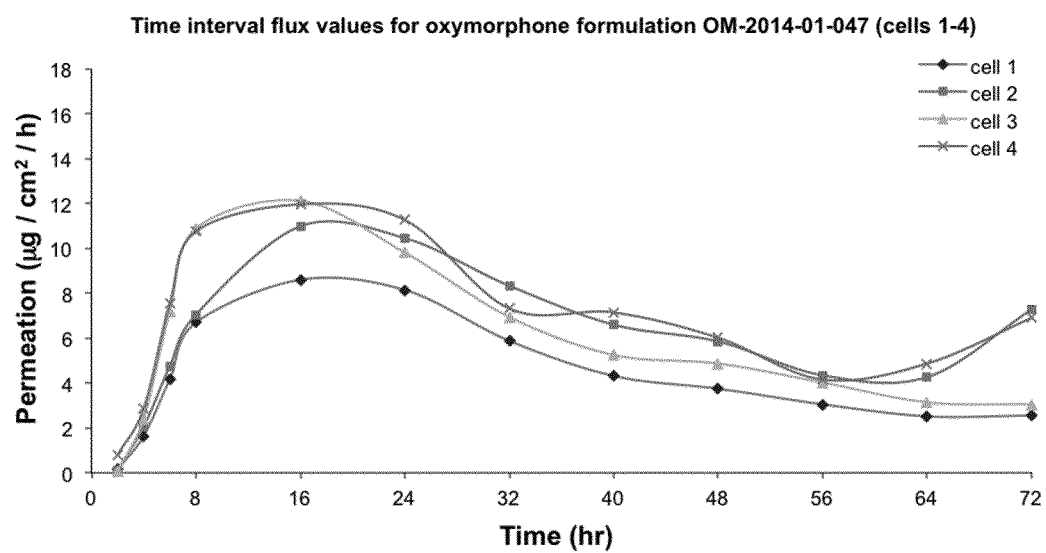
FIG. 21 shows the representative human skin permeation profile of oxymorphone formulations, OM-2014-01-047 (n=4).
Figure 22:
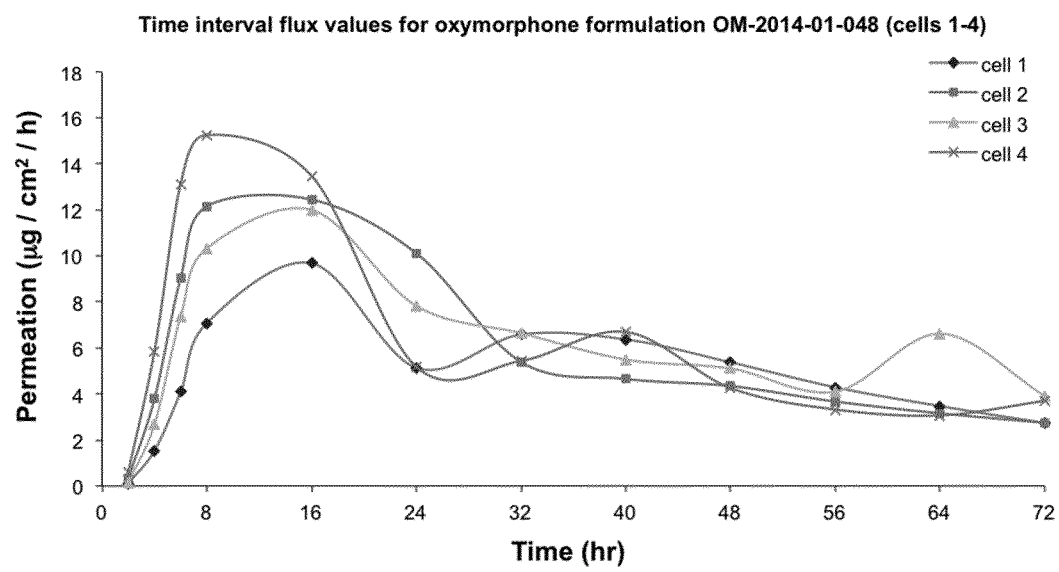
FIG. 22 shows the representative human skin permeation profile of oxymorphone formulations, OM-2014-01-048 (n=4).

Formulations OM-01-047 and OM-01-048 were also tested on human skin. The results are summarised in FIGS. 21 and 22.

Example 2

Abuse-deterrent Layer

Typical Preparation of Abuse-Deterrent Formulations

The following series of steps provide a typical protocol for the preparation of the naloxone/naltrexone abuse-deterrent formulations forming part of the invention (in this specific example, the preparation of a 10% 1:1 naloxone base:naloxone.HCl matrix layer). Materials and amounts may vary depending on specific composition of formulations.

Using 12 M (37% HCl, USP) and 200 proof ethanol (USP), prepare a stock solution of 0.3 M HCl in ethanol.
   a. Using a 25 mL volumetric pipet, transfer exactly 25.00 mL of 12 M HCl to a 1000 mL volumetric flask and dilute to the mark with 200 proof ethanol.
   b. Cap the solution and place in the 4° C. refrigerator when not in use.
   c. The solution will prepare up to 2 kg of the formulation described below.

Preparation of abuse-deterrent formulation (1 kg batch size):
1. Weigh 100 g (305 mmol) naloxone base into a mixing vessel (10% w/w).
2. Tare weight and add 50 g of polyvinylpyrolidone K30 to the vessel (5% w/w).
3. Pipet 500 mL of 0.3 M HCl (150 mmol) in ethanol into the vessel and begin blending.
4. Mix until suspension is blended well.
5. Add 1.574 kg Duro-Tak® 9301 (non-volatile content (NVC) 41.3%) (65% w/w).
6. Tare and add 1.333 kg 1:9 hydroxypropylcellulose:ethylcellulose (NVC 15%) (20% w/w).
7. Blend until a homogenous suspension is achieved.
8. Extrude at 30 mil wet thickness onto 3M™ Scotchpak™ 9744 release liner and air dry for 30 minutes at 25° C.
9. Oven dry at 90° C. for 15 minutes.
10. Laminate with 3M™ Scotchpak™ 9730 backing membrane and reroll the sample until assembly.
11. Store desiccated until ready for use.

Naloxone/Naltrexone Formulations

The composition of exemplary naloxone and naltrexone formulations are summarized below:

| NLX-2014-01-001 |
|---|
| 10% Naloxone•HCl |
| 20% Ethyl Cellulose:Hydroxypropyl Cellulose (1:9) |
| 70% Dow Corning® BIO-PSA 7-4302 |
| 1000 μL Ethanol |

| NLX-2014-01-003 |
|---|
| 10% Naloxone•HCl |
| 20% Ethyl Cellulose:Hydroxypropyl Cellulose (1:9) |
| 3% Polyvinylpyrollidone [PVP-K30] (MW 30,000) |
| 67% Dow Corning® BIO-PSA 7-4302 |
| 1000 μL Ethanol |

| NLX-2014-01-005 |
|---|
| 10% Naloxone•HCl |
| 20% Ethyl Cellulose:Hydroxypropyl Cellulose (1:9) |
| 5% Polyvinylpyrollidone [PVP-K30] (MW 30,000) |
| 65% Duro-Tak® 9301 |
| 1000 μL Ethanol |

| NLX-2014-01-007 |
|---|
| 10% Naloxone•HCl |
| 20% Ethyl Cellulose:Hydroxypropyl Cellulose (1:9) |
| 7.5% Dow® Dipropylene Glycol LO+ |
| 62.5% Duro-Tak® 9301 |
| 1000 μL Ethanol |

| NLX-2014-01-009 |
|---|
| 10% Naloxone•HCl |
| 20% Ethyl Cellulose:Hydroxypropyl Cellulose (1:9) |
| 5% Dow® Dipropylene Glycol LO+ |
| 65% Duro-Tak® 900A |
| 500 μL Ethanol |

| NLX-2014-01-011 |
|---|
| 10% Naloxone•HCl |
| 20% Ethyl Cellulose:Hydroxypropyl Cellulose (1:9) |
| 5% Polyvinylpyrollidone [PVP-K30] (MW 30,000) |
| 65% Duro-Tak® 9301 |
| 500 μL Ethanol |

| NTX-2014-01-001 |
|---|
| 5% Naltrexone•HCl |
| 5% Naltrexone Base |
| 20% Ethyl Cellulose:Hydroxypropyl Cellulose (1:9) |
| 5% Polyvinylpyrollidone [PVP-K30] (MW 30,000) |
| 65% Duro-Tak® 9301 |
| 500 μL Ethanol |

| NLX-2014-01-002 |
|---|
| Same as 001 with a new batch EC:HPC |

| NLX-2014-01-004 |
|---|
| 10% Naloxone•HCl |
| 20% Ethyl Cellulose:Hydroxypropyl Cellulose (1:9) |
| 5% Polyvinylpyrollidone [PVP-K30] (MW 30,000) |
| 65% Dow Corning® BIO-PSA 7-4302 |
| 1000 μL Ethanol |

NLX-2014-01-006

10% Naloxone•HCl
20% Ethyl Cellulose:Hydroxypropyl Cellulose (1:9)
5% Dow ® Dipropylene Glycol LO+
65% Duro-Tak ® 9301
1000 µL Ethanol

NLX-2014-01-008

10% Naloxone•HCl
20% Ethyl Cellulose:Hydroxypropyl Cellulose (1:9)
5% Dow ® Dipropylene Glycol LO+
65% Duro-Tak ® 9301
500 µL Ethanol

NLX-2014-01-010

10% Naloxone•HCl
20% Ethyl Cellulose:Hydroxypropyl Cellulose (1:9)
3% Polyvinylpyrrollidone [PVP-K30] (MW 30,000)
67% Duro-Tak ® 9301
500 µL Ethanol

NLX-2014-01-012

5% Naloxone•HCl
5% Naloxone Base
20% Ethyl Cellulose:Hydroxypropyl Cellulose (1:9)
5% Polyvinylpyrrollidone [PVP-K30] (MW 30,000)
65% Duro-Tak ® 9301
1000 µL Ethanol A variety if adhesive systems, enhancers and cosolvents were employed to generate different antagonist formulations.

All formulations showed appropriate to excellent dispersion of the antagonist.

Abuse-deterrent Formulation Test Data

Table 8 below shows molar release ratios of oxymorphone:naltrexone (4:1 minimal requirement) from the 5.0% oxymorphone (OM-2014-01-025) prototype abuse deterrent transdermal delivery system (NTX-2014-01-001) in water, ethanol, and acetone. A value less than 4 indicates that narcotic blockade would be achieved.

TABLE 8

Molar release ratios of oxymorphone:naltrexone (4:1 minimal requirement) from the 5.0% oxymorphone (OM-2014-01-025) prototype abuse deterrent transdermal delivery system (NTX-2014-01-001) in water, ethanol, and acetone

| Time points (min) | Water | Ethanol | Acetone |
| --- | --- | --- | --- |
| 2 | 0.4 | 2.4 | 2.4 |
| 5 | 0.3 | 2.2 | 1.7 |
| 10 | 0.4 | 1.9 | 0.7 |
| 20 | 0.6 | 1.8 | 0.6 |
| 30 | 1.7 | 1.7 | 0.6 |
| 60 | 0.5 | 1.5 | 0.6 |

Table 9 below shows molar release ratios of oxymorphone:naltrexone (4:1 minimal requirement) from the 5.0% oxymorphone (OM-2014-01-025) prototype abuse deterrent transdermal delivery system (NTX-2014-01-001) under chewing simulation in phosphate buffer pH 6.3

TABLE 9

Molar release ratios of oxymorphone:naltrexone (4:1 minimal requirement) from the 5.0% oxymorphone (OM-2014-01-025) prototype abuse deterrent transdermal delivery system (NTX-2014-01-001) under chewing simulation in phosphate buffer pH 6.3

| Time points (min) | Chewing |
| --- | --- |
| 1 | 1.2 |
| 2 | 1.2 |
| 5 | 1.1 |
| 10 | 1.1 |
| 15 | 1.0 |

Table 10. Molar release ratios of oxymorphone:naltrexone (4:1 minimal requirement) from the 3.5% oxymorphone (OM-2014-01-024) prototype abuse deterrent transdermal delivery system (NTX-2014-01-001) in water, ethanol, and acetone

TABLE 10

Molar release ratios of oxymorphone:naltrexone (4:1 minimal requirement) from the 3.5% oxymorphone (OM-2014-01-024) prototype abuse deterrent transdermal delivery system (NTX-2014-01-001) in water, ethanol, and acetone

| Time points (min) | Water | Ethanol | Acetone |
| --- | --- | --- | --- |
| 2 | 0.3 | 1.6 | 1.6 |
| 5 | 0.2 | 1.3 | 0.6 |
| 10 | 0.2 | 1.2 | 0.4 |
| 20 | 0.2 | 1.2 | 0.4 |
| 30 | 0.3 | 1.2 | 0.3 |
| 60 | 0.3 | 1.1 | 0.4 |

Table 11. Molar release ratios of oxymorphone:naltrexone (4:1 minimal requirement) from the 3.5% oxymorphone (OM-2014-01-024) prototype abuse deterrent transdermal delivery system (NTX-2014-01-001) under chewing simulation in phosphate buffer pH 6.3

TABLE 11

Molar release ratios of oxymorphone:naltrexone (4:1 minimal requirement) from the 3.5% oxymorphone (OM-2014-01-024) prototype abuse deterrent transdermal delivery system (NTX-2014-01-001) under chewing simulation in phosphate buffer pH 6.3

| Time points (min) | Chewing |
| --- | --- |
| 1 | 0.5 |
| 2 | 0.6 |
| 5 | 0.5 |
| 10 | 0.4 |
| 15 | 0.4 |

The ability of abuse-deterrent layer formulations to migrate into the oxymorphone layer was investigated. A placebo oxymorphone layer was prepared and two abuse-deterrent formulations (NLX-2014-01-011 and NLX-2014-01-012) were tested with different separating layers. The appearance of both formulations was uniform and aesthetically pleasing. When assembled, no distinguishable layers could be observed and the layers themselves were inseparable. Patches of size 0.95 cm$^2$ patches were punched out from the release liner side of the assembled roll. The results of the abuse-deterrent permeation studies are presented in Table 12 below.

TABLE 12

Permeation of abuse-deterrent formulations into opioid layer

| Formulation | Flux µg/cm²/h | Cum. Permeation (nmol) | Lag time (h) |
|---|---|---|---|
| NLX-2014-01-012 with cellulose spacing membrane (n = 4) | 0.15 ± 0.07 | 15.1 ± 5.5 | 5.4 ± 4.2 |
| NLX-2014-01-011 with cellulose spacing membrane (n = 4) | 0.05 ± 0.06* | 5.5 ± 6.4* | 0.3 ± 0.6* |
| NLX-2014-01-012 with Lydall Solupor spacing membrane (n = 3) | 0.2** | 12.36** | 17.25** |

*Indicates that 2 of the four cells analysed showed no permeation of naloxone over 72 h but were averaged together with the two cells that did have the presence of naloxone. Overall permeation was miniscule during the 72 h study.
**Indicates that two of the three cells have no detection of naloxone over 72 h diffusion study. The flux, cumulative permeation and lag time value shown is from the one cell containing naloxone.

Insofar as NLX-2014-01-011 is concerned, while two cells did show permeation from the abuse deterrent layer, this was probably due to the abuse deterrent layer contacting the skin, as by the end of the experiment almost no permeation was observed. It was therefore concluded that naloxone hydrochloride is largely impermeable in the system. When using a Lydall Solupor 10P05A separator, which is a commercially available microporous membrane, two of the three cells showed no permeation whatsoever. The Lydall membrane limited naloxone permeation through the skin whereas the same formulation containing 5% naloxone base and 5% naloxone hydrochloride tested with the cellulose membrane showed some permeation through all four cells.

Further Abuse Deterrent Studies

Naloxone hydrochloride (NLX) is commonly used to overcome sedation and overdose of opiate abuse including oxymorphone. In 1990, a study to overcome sedation in dogs showed that a 4.5 mg intravenous dose was reversed by a 1.2 mg intravenous dose of naloxone (Vet Surg. 1990 Sep-Oct;19(5):398-403).

Converting the agonist and antagonist dose to mol amounts provides information to calculate a naloxone:oxymorphone ratio required for abuse deterrence. The mol amounts administered in dogs were 3.7 µmol and 14.9 µmol of naloxone and oxymorphone, respectively. Thus, the target release ratio of naloxone:oxymorphone is 1:4.

The formulation to test the abuse deterrent release characteristics containing NLX and OXY consisted of formulation OM-2014-01-014, a cellulose based polymeric film matrix and a NLX containing matrix as described.

Hydroxyproyl cellulose (HPC) solution was prepared by dissolving 15% of polymer (Klucel® EF PH) in ethanol. Another solution of 15% ethyl cellulose (EC) was prepared by dissolving the polymer (EC-N50 PH) in chloroform:methanol (8:2). Both solutions were allowed to stir for 24 h to insure complete dissolution in the various solvent systems. These stock solutions were used to prepare both the polymeric film layer and NLX containing layer.

A polymeric film that separated the OXY containing layer from the NLX containing matrix was prepared by adding 40% w/w polyethylene glycol (PEG) 400 to a 60% mixture of EC:HPC (8:2). The solution was mixed thoroughly, cast onto a release liner at wet thickness of 20 mil, and dried.

The antagonist layer containing NLX was prepared by dispersing 10% w/w NLX in 20% w/w EC:HPC (9:1) and 70% w/w Dow Corning® BIO-PSA 7-4302. An additional 0.3 mL/g of ethanol was added to enhance dispersion during mixing. The solution was cast at 20 mil thickness onto release liner and dried.

Figure 24:
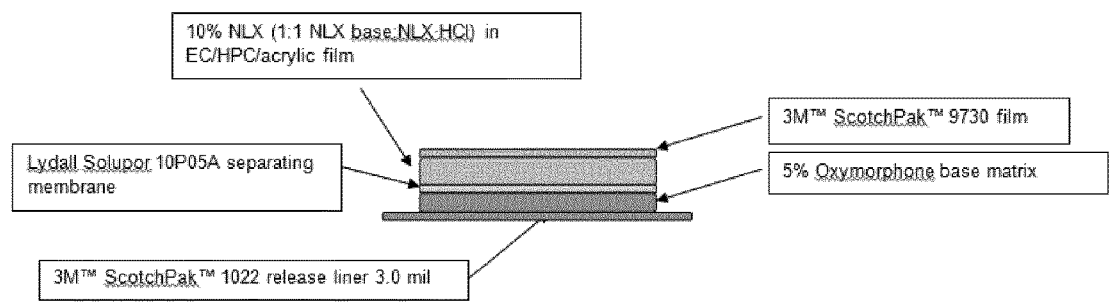
FIG. 24 shows an exemplary assembled abuse-deterrent transdermal patch (not to scale).

OM-2014-01-014 was laminated to the polymeric film containing no drug and the NLX layer laminated to backing membrane ScotchPak™ 9730. Finally, the NLX-backing membrane portion was laminated to the polymeric film OM-2014-01-014 portion to create a tri-layered abuse deterrent system. Patch schematic is shown in FIG. 24.

For the abuse deterrence studies, a 1.0 cm² patch of the abuse deterrent system containing 5% OXY and 10% NLX was placed in solvent systems commonly used to extract opiates under abuse conditions. Each patch was placed in a container with 10 mL of water, ethanol, acetone, or pH 6.3 phosphate buffer and placed on the orbital shaker. The phosphate buffer was employed to represent the pH of saliva. A glass rod was used to grind the patch (duration of the study) while in the solution to simulate chewing. Tables 13 and 14 show the release ratios of NLX:OXY observed in the abuse media over time.

TABLE 13

Molar release ratios of NLX:OXY from the prototype abuse deterrent transdermal delivery system in water, ethanol, and acetone

| Time points (min) | Water | Ethanol | Acetone |
|---|---|---|---|
| 2 | 7.9:1 | 0.9:1 | 0.8:1 |
| 5 | 6.1:1 | 1.3:1 | 1.1:1 |
| 10 | 7.4:1 | 2.0:1 | 1.8:1 |
| 20 | 10.7:1 | 1.4:1 | 1.9:1 |
| 30 | 11.2:1 | 4.5:1 | 1.8:1 |
| 60 | 4.3:1 | 3.8:1 | 2.0:1 |

TABLE 14

Molar release ratios of NLX:OXY from the prototype abuse deterrent transdermal delivery system under chewing simulation in phosphate buffer pH 6.3

| Time points (min) | Chewing |
|---|---|
| 1 | 18.1:1 |
| 2 | 17.3:1 |
| 5 | 25.9:1 |
| 10 | 20.5:1 |
| 15 | 19.5:1 |

In all abuse media tested the target ratio was achieved initially and throughout the period of extraction. The ratios observed were much greater than the 1:4 NLX:OXY ratio desired in even organic extraction media. This observance allows the formulation to be either held at a 10% w/w NLX drug load in the abuse deterrent layer or explore further formulations that contain less than 10% drug load and still achieve adequate release ratios that would potentially provide narcotic blockade.

Example 3

Transdermal Patch

Patch Assembly

The patch assembly process is a one step process that brings together rolls of: 1) an oxymorphone matrix layer attached to a release liner (e.g. 3M™ Scotchpak™ 1022 release liner), 2) Lydall Solupor 10P05A separating membrane (commercially purchased with DMF on file) and 3) an abuse-deterrent layer (e.g. a 10% 1:1 naloxone base:naloxone.HCl abuse deterrent layer).

Figure 23:
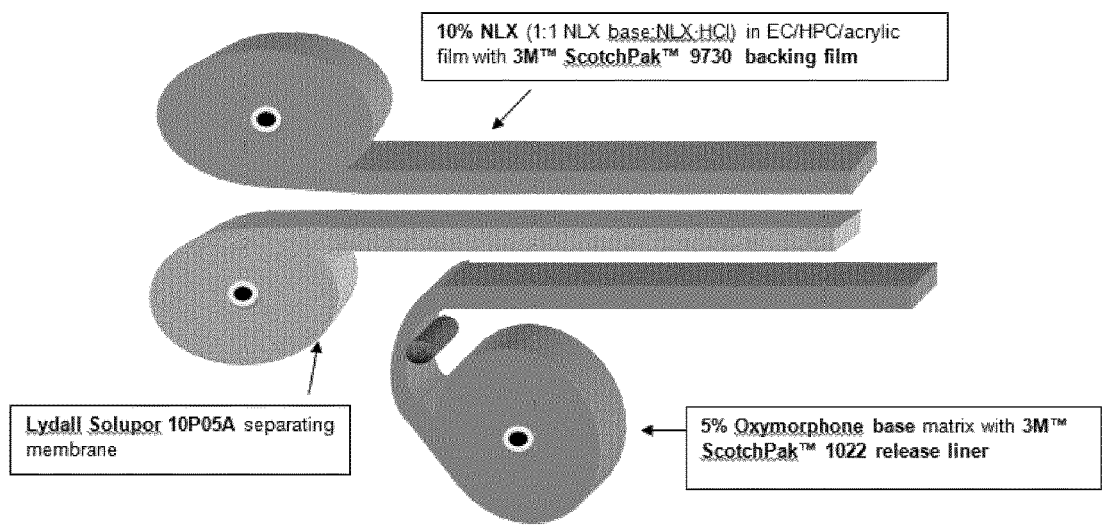
FIG. 23 shows an exemplary abuse-deterrent transdermal patch assembly protocol.

In a fully automated manufacturing process, the three rolls are placed onto a continuous manufacturing platform and then laminated together as shown in FIG. 23. Once laminated, the laminate is then cut to the appropriate size for the dosage form (see FIG. 24) and finally packaged.

Particular embodiments of the invention are described in the following numbered paragraphs:
1. A transdermal patch comprising a first layer as defined herein and wherein the opioid analgesic present in said layer is oxymorphone, or a pharmaceutically acceptable salt thereof.
2. A transdermal patch according to paragraph 1, wherein the opioid analgesic is present at an amount of 1-10% w/w.
3. A transdermal patch according to paragraph 2, wherein the opioid analgesic is present at an amount of 4-7% w/w in said layer.
4. A transdermal patch according to any one of paragraph 1 to 3, wherein the opioid analgesic is present in a non-salt form, i.e. as a free base or acid.
5. A transdermal patch according to any one of paragraphs 1 to 4, wherein the total amount of adhesive will constitute between 58 and 99% w/w of the first and second layers respectively.
6. A transdermal patch according to any one of paragraphs 1 to 5, wherein the adhesive is selected from acrylate/polyacrylate materials, rubbers and silicones or mixtures thereof.
7. A transdermal patch according to any one of paragraphs 1 to 6, wherein the adhesive is a mixture of an acrylate/polyacrylate adhesive and a silicone adhesive.
8. A transdermal patch according to any one of paragraphs 1 to 7, wherein the first layer comprises a penetration enhancer.
9. A transdermal patch according to paragraph 8, wherein the penetration enhancer is present in an amount of 2-12% w/w of the first layer.
10. A transdermal patch according to paragraph 8 or paragraph 9, wherein the penetration enhancer is oleic acid.

The invention claimed is:
1. A transdermal patch comprising a multilaminate, said multilaminate comprising:
   (i) a first layer comprising an opioid analgesic compound, or a pharmaceutically acceptable salt thereof, and a pharmaceutically acceptable pressure sensitive adhesive;
   (ii) a second layer comprising an opioid antagonist, or a pharmaceutically acceptable salt thereof, and a pharmaceutically acceptable adhesive; and
   (iii) a barrier layer disposed between the first and second layers, and wherein the barrier layer substantially prevents the opioid antagonist diffusing from the second layer to the first layer during use, and wherein the barrier layer is a microporous ultra high density polyethylene (UHDPE) material;
   and wherein a proportion of the opioid antagonist in the second layer is present in the form of a pharmaceutically acceptable salt and a proportion of the opioid antagonist is present in a non-salt form.
2. A transdermal patch according to claim 1, wherein 5-95% w/w or 30-70% w/w of the total opioid antagonist present in the second layer is in the form of a pharmaceutically acceptable salt and the remainder is in a non-salt form.
3. A transdermal patch according to claim 1, wherein the opioid analgesic is selected from morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine and buprenorphine, fentanyl, pethidine, levorphanol, methadone, tramadol and dextropropoxyphene.
4. A transdermal patch according to claim 1, wherein the opioid analgesic is oxymorphone, or a pharmaceutically acceptable salt thereof.
5. A transdermal patch according to claim 1, wherein the opioid analgesic is present at an amount of 1-10% w/w or 4-7% w/w in the first layer.
6. A transdermal patch according to claim 1, wherein the opioid analgesic is present in a non-salt form.
7. A transdermal patch according to claim 1, wherein the total amount of adhesive will constitute between 58 and 99% w/w of the first and second layers respectively.
8. A transdermal patch according to claim 1, wherein the adhesive is selected from acrylate/polyacrylate materials, rubbers and silicones or mixtures thereof.
9. A transdermal patch according to claim 1, wherein the adhesive is a mixture of an acrylate/polyacrylate adhesive and a silicone adhesive.
10. A transdermal patch according to claim 1, wherein the first layer comprises a penetration enhancer.
11. A transdermal patch according to claim 10, wherein the penetration enhancer is present in an amount of 2-12% w/w of the first layer.
12. A transdermal patch according to claim 10, wherein the penetration enhancer is oleic acid.
13. A transdermal patch according to claim 1, wherein the opioid antagonist in the second layer is selected from naltrexone ("NTX"), naloxone ("NLX") or nalmefene.
14. A transdermal patch according to claim 1, wherein the opioid antagonist is present in an amount of 1-20% w/w of the second layer.
15. A transdermal patch according to claim 1, wherein the second layer further comprises polyvinylpyrollidinone in an amount of 0.5 to 15% w/w of the second layer.
16. A transdermal patch according to claim 15, wherein the polyvinylpyrollidinone is polyvinylpyrollidone K30.
17. A transdermal patch according to claim 1, wherein the second layer further comprises a cellulose component in an amount of 5 to 25% w/w of the second layer.
18. A transdermal patch according to claim 1, wherein the second layer further comprises a hydrophilic material in an amount of 1 to 10% w/w of the second layer.
19. A transdermal patch according to claim 18, wherein the hydrophilic material is propylene glycol or dipropylene glycol.
20. A transdermal patch according to claim 1, wherein a proportion of the opioid antagonist in the second layer is present in the form of a pharmaceutically acceptable salt and a proportion of the opioid antagonist is present as a free base.
21. A method of treating a condition selected from the group consisting of opioid dependence, alcohol dependence, polydrug addiction, pain, cocaine addiction, eating disorders (e.g., binge eating) and treatment-resistant depression in a subject in need of such treatment, said method comprising administering a transdermal patch according to claim 1 to the skin of the subject.

* * * * *